(12) United States Patent  (10) Patent No.: US 7,766,833 B2
Lee et al.  (45) Date of Patent: Aug. 3, 2010

(54) ABLATION ARRAY HAVING INDEPENDENTLY ACTIVATED ABLATION ELEMENTS

(75) Inventors: Warren Lee, Schenectady, NY (US); Mirsaid Seyed-Bolorforosh, Schenectady, NY (US); Douglas Glenn Wildes, Ballston Lake, NY (US)

(73) Assignee: General Electric Company, Niskayuna, NY (US)

( * ) Notice: Subject to any disclaimer, the term of this patent is extended or adjusted under 35 U.S.C. 154(b) by 739 days.

(21) Appl. No.: 11/276,259

(22) Filed: Feb. 21, 2006

(65) Prior Publication Data

US 2007/0129633 A1 Jun. 7, 2007

Related U.S. Application Data

(60) Provisional application No. 60/739,800, filed on Nov. 23, 2005.

(51) Int. Cl.
*A61B 8/00* (2006.01)
*A61B 8/14* (2006.01)
*A61H 1/00* (2006.01)

(52) U.S. Cl. ............ 600/439; 600/459; 600/471; 601/2

(58) Field of Classification Search .......... 600/439, 600/445, 459, 447, 6, 9, 10, 11, 471; 601/2
See application file for complete search history.

(56) References Cited

U.S. PATENT DOCUMENTS

| 4,932,414 | A | * | 6/1990 | Coleman et al. ............ 600/445 |
| 5,492,126 | A | | 2/1996 | Hennige et al. |
| 5,558,092 | A | * | 9/1996 | Unger et al. ................. 600/439 |
| 5,720,287 | A | | 2/1998 | Chapelon et al. |
| 5,769,790 | A | | 6/1998 | Watkins et al. |
| 5,817,021 | A | | 10/1998 | Reichenberger |
| 5,873,828 | A | | 2/1999 | Fujio et al. |
| 6,039,689 | A | * | 3/2000 | Lizzi ......................... 600/439 |
| 6,246,898 | B1 | * | 6/2001 | Vesely et al. ................ 600/424 |
| 6,425,867 | B1 | | 7/2002 | Vaezy et al. |
| 6,605,084 | B2 | * | 8/2003 | Acker et al. .................. 606/28 |
| 6,626,855 | B1 | | 9/2003 | Weng et al. |
| 6,685,639 | B1 | | 2/2004 | Wang et al. |
| 6,746,401 | B2 | * | 6/2004 | Panescu ..................... 600/439 |
| 6,761,716 | B2 | * | 7/2004 | Kadhiresan et al. .......... 606/34 |
| 7,063,666 | B2 | | 6/2006 | Weng et al. |

(Continued)

OTHER PUBLICATIONS

U.S. Appl. No. 11/276,258.*
Kenneth L. Gentry et al., Finite Element Analysis of Temperature Rise from an Integrated Catheter for 3-D Intracardiac Echocardiography and Ultrasound Ablation, IEEE, Aug. 24, 2004, U2-B-I, 18 pages.
Netherlands Search Report—Jan. 24, 2008.
Co-pending U.S. Appl. No. 11/225,331, filed Sep. 13, 2005, entitled "Automated Imaging and Therapy System".
Co-pending U.S. Appl. No. 12/327,171, filed Dec. 3, 2008, entitled "Integrated Ultrasound Imaging and Ablation Probe".

*Primary Examiner*—Eric F Winakur
*Assistant Examiner*—Katherine L Fernandez
(74) *Attorney, Agent, or Firm*—Scott J. Asmus

(57) ABSTRACT

A system for imaging and providing therapy to one or more regions of interest is presented. The system includes an imaging and therapy catheter configured to image an anatomical region to facilitate assessing need for therapy in one or more regions within the anatomical region and delivering therapy to the one or more regions of interest within the anatomical region. The catheter includes a therapy device having a plurality of independently controllable therapy elements. The independence of the therapy elements is exploited when multiple regions are to receive therapy simultaneously or at a given catheter position within a subject.

38 Claims, 13 Drawing Sheets

U.S. PATENT DOCUMENTS

| | | |
|---|---|---|
| 2002/0082503 A1* | 6/2002 | Chandrasekaran et al. .. 600/466 |
| 2002/0107447 A1* | 8/2002 | Suorsa et al. ............... 600/466 |
| 2003/0208123 A1* | 11/2003 | Panescu ...................... 600/431 |
| 2004/0254569 A1* | 12/2004 | Brosch et al. ................. 606/27 |
| 2005/0119576 A1* | 6/2005 | Li ............................... 600/459 |
| 2005/0215899 A1* | 9/2005 | Trahey et al. ............... 600/439 |
| 2005/0240125 A1* | 10/2005 | Makin et al. .................... 601/2 |
| 2005/0267453 A1* | 12/2005 | Wong et al. ................... 606/27 |

* cited by examiner

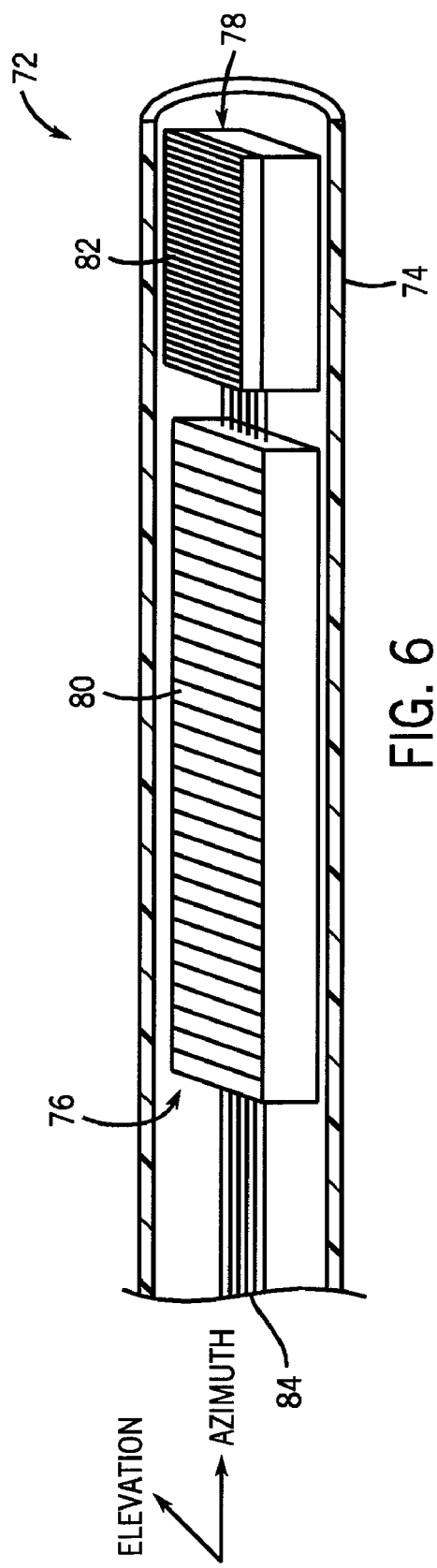
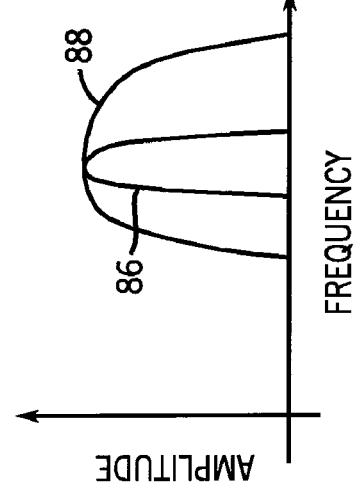
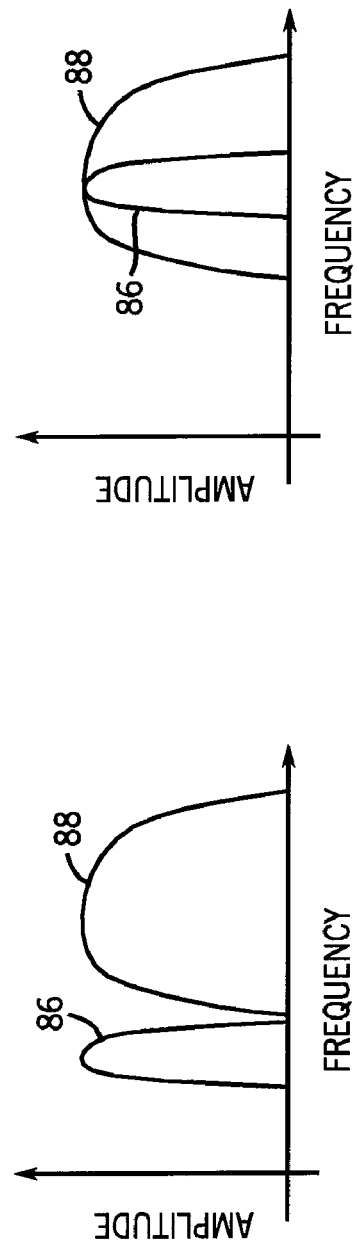

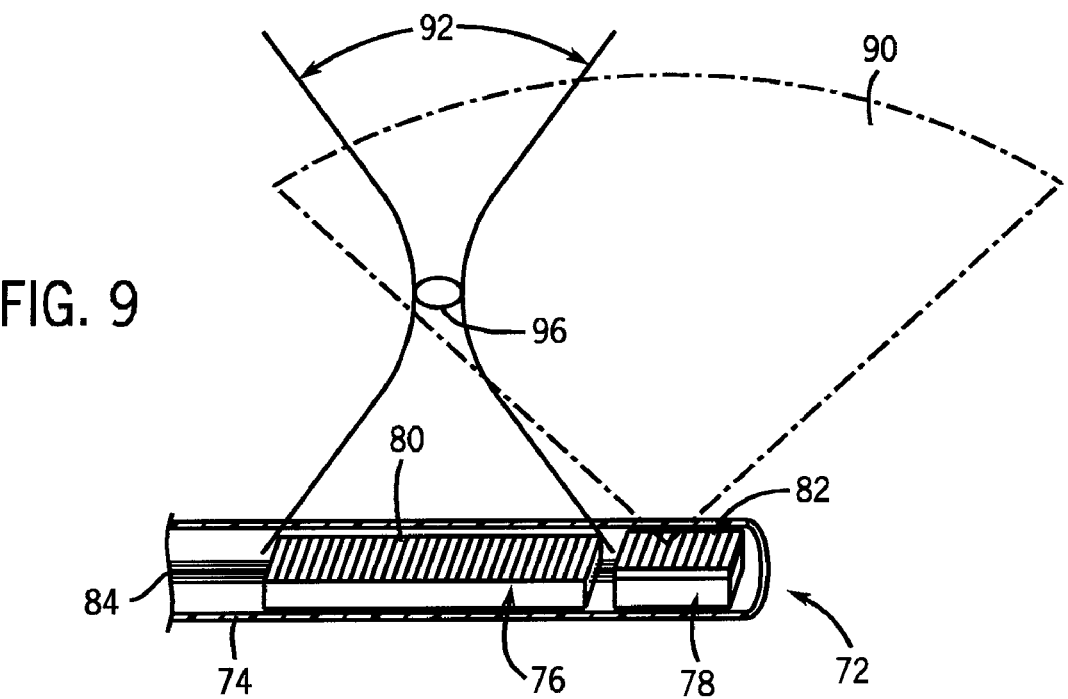
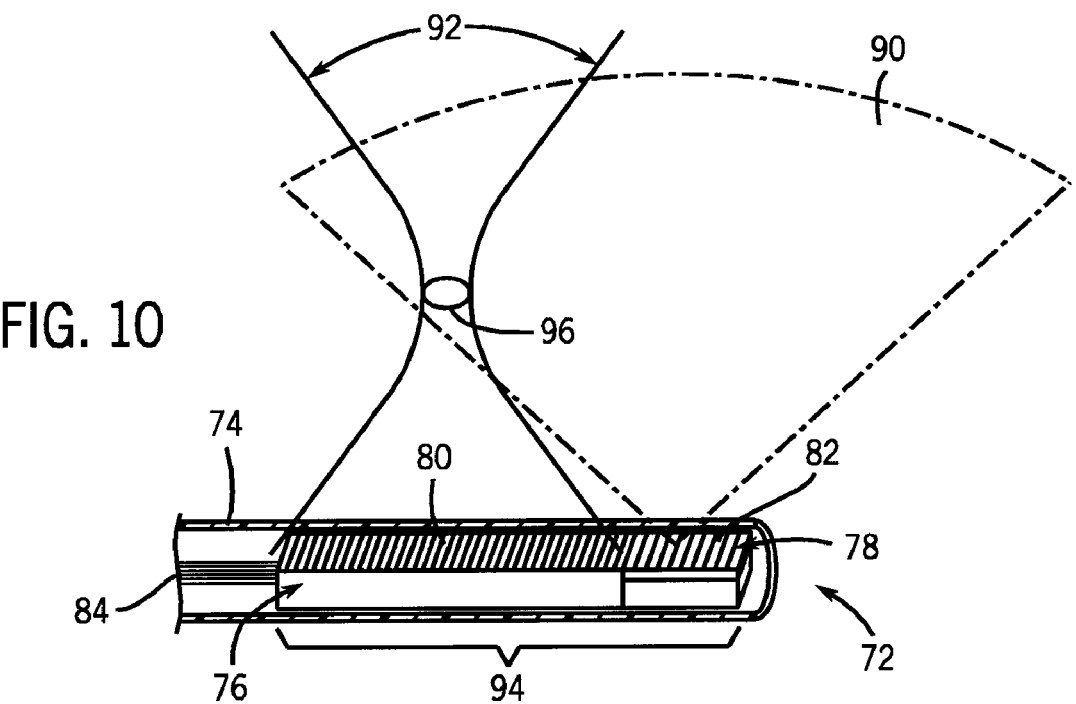

ABLATION ARRAY HAVING INDEPENDENTLY ACTIVATED ABLATION ELEMENTS

CROSS-REFERENCE TO RELATED APPLICATION

The present invention claims the benefit of provisional application U.S. Ser. No. 60/739,800, filed Nov. 23, 2005.

BACKGROUND OF THE INVENTION

The invention relates generally to diagnostic imaging, and more particularly, to an ablation array having independently activated ablation elements. The invention is further related to control of such an ablation array to ablate multiple ablation points simultaneously, create a linear or curvilinear ablation lesion, or ablate multiple ablation points at a given catheter position.

Heart rhythm problems or cardiac arrhythmias are a major cause of mortality and morbidity. Atrial fibrillation is one of the most common sustained cardiac arrhythmias encountered in clinical practice. Cardiac electrophysiology has evolved into a clinical tool to diagnose and treat these cardiac arrhythmias. As will be appreciated, during electrophysiological studies, multipolar catheters are positioned inside the anatomy, such as the heart, and electrical recordings are made from the different chambers of the heart. Further, catheter-based ablation therapies have been employed for the treatment of atrial fibrillation.

Conventional techniques utilize radio frequency (RF) catheter ablation for the treatment of atrial fibrillation. Currently, catheter placement within the anatomy is typically performed under fluoroscopic guidance. Intracardiac echocardiography (ICE) has also been employed during RF catheter ablation procedures. Additionally, the ablation procedure may necessitate the use of a multitude of devices, such as a catheter to form an electroanatomical map of the anatomy, such as the heart, a catheter to deliver the RF ablation, a catheter to monitor the electrical activity of the heart, and an imaging catheter. A drawback of these techniques however is that these procedures are extremely tedious requiring considerable manpower, time and expense. Further, the long procedure times associated with the currently available catheter-based ablation techniques increase the risks associated with long term exposure to ionizing radiation to the patient as well as medical personnel.

Additionally, with RF ablation, the tip of the catheter is disadvantageously required to be in direct contact with each of the regions of the anatomy to be ablated. RF energy is then used to cauterize the identified ablation sites. Further, in RF ablation techniques, the catheter is typically placed under fluoroscopic guidance. However, fluoroscopic techniques disadvantageously suffer from drawbacks, such as difficulty in visualizing soft tissues, which may result in a less precise definition of a therapy pathway. Consequently, these RF ablation techniques typically result in greater collateral damage to tissue surrounding the ablation sites. In addition, RF ablation is associated with stenosis of the pulmonary vein.

Moreover, a pre-case computed tomography (CT) and/or magnetic resonance imaging (MRI) as well as electroanatomical (EA) mapping systems may be employed to acquire static, anatomical information that may be used to guide the ablation procedure. However, these systems disadvantageously provide only static images and are inherently unfavorable for imaging dynamic structures such as the heart.

Another issue frustrating intravenous and intra-arterial ablation is the non-integration between ultrasonic imaging arrays and ablation arrays, each of which are positioned in a body via separate catheters. As described above, this typically results in multiple catheters being disposed in a patient for a single interventional procedure. This is particularly prevalent in ICE. Specifically, it is not uncommon for some ICE procedures to utilize three to four catheters inside the heart chambers in the course of the procedures. Adding to the multiplicity of catheters is that catheters used to deliver RF ablation energy are separate from the catheter used to visualize the ablation catheters and target anatomy. This poses two general drawbacks. First, by separating the imaging and ablation catheters, the physician must use a 2D imaging device to guide an independent catheter being manipulated in three dimensions. Understandably, this can be difficult and time-consuming. Second, conventional ablation techniques utilize RF ablation catheters, which, as described above, require the physician to physically contact each desired ablation point. As a typical ICE procedure will include 100-200 ablation points, the ablation process can become quite tedious and lengthy. In addition to ICE, the same or similar drawbacks are also experienced in transesophageal echocardiography (TEE), laparoscopy, arthroscopy, and other procedures characterized by a disintegration of imaging and ablation devices.

Additionally, conventional ablation devices are characterized by an array of globally controlled ablation elements. That is, all of the ablation elements of the ablation array are activated/deactivated as a group. This results in an ablation beam defined by a high amplitude main lobe and a series of generally off-centered, low amplitude secondary lobes. As a result of this conventional construction and use, only a single ablation point can be ablated at a time. Since most ablation procedures involve approximately 100-200 ablation points, one-at-time ablation can be quite time consuming and tedious.

There is therefore a need for an integrated imaging and ablation catheter that provides intracorporeal imaging and that also allows for the ablation, assessment, and reablation, if necessary, without ablation point contact. It would also be desirable to have an ablation device capable of ablating multiple ablation points simultaneously.

BRIEF DESCRIPTION OF THE INVENTION

The present invention is directed to a therapy device having an array of independently controllable therapy elements that overcomes the aforementioned drawbacks. The therapy device includes multiple therapy elements that may be independently and selectively activated to perform multiple therapy procedures simultaneously, perform multiple therapy procedures from a given position of the therapy device, or, in the context of an ablation device, create a linear or curvilinear ablation lesion. In one aspect, the therapy device together with an imaging device, such as an ultrasound transducer, is arranged along a long axis of a catheter that is translatable intracorporeally within a subject, e.g. medical patient.

Therefore, in accordance with one aspect of the invention, an ablation device is presented. The ablation device includes an array of ablation elements that are independently controllable. As such, the ablation device further includes a controller connected to the ablation elements and configured to apply different excitation waveforms to different ablation elements during a given ablation procedure. The excitation waveforms may, for example, differ in frequency, phase, time delay, and/or amplitude.

In accordance with another aspect, the invention includes an integrated therapy and imaging catheter. The catheter is constructed to have an ultrasound transducer and an ablation array having a plurality of ablation elements. The ablation array is constructed such that the ablation elements are selectively activated for multi-lesion ablation.

According to yet another aspect of the invention, an imaging and ablation system is disclosed and comprises a display configured to display images, an imaging device configured to acquire images, and an ablation device having a plurality of independently controllable ablation elements. A controller is operably connected to the imaging device to control image acquisition and is operably connected to the ablation device to selectively activate the plurality of independently controllable ablation elements for a given ablation procedure.

According to a further aspect, the invention includes an ablation device having a plurality of ablation elements. The device includes a controller connected to define a first set and a second set of ablation elements for a given ablation. The first set of ablation elements comprising different ablation elements than the second set.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings:

FIG. 6 shows an integrated imaging and therapy catheter wherein the therapy array extends along the catheter long axis in accordance with aspects of the present invention.

FIG. 7 illustrates distinct operating frequencies of an exemplary therapy array and exemplary imaging array.

FIG. 8 illustrates overlapping operating frequencies of an exemplary therapy array and exemplary imaging array.

FIG. 9 illustrates an exemplary catheter in accordance with aspects of the present invention wherein the therapy and imaging arrays are separate arrays housed within the catheter.

FIG. 10 illustrates another exemplary catheter in accordance with aspects of the present invention wherein the therapy and imaging arrays are subsets of a common array and housed within the catheter.

DETAILED DESCRIPTION OF THE PREFERRED EMBODIMENT

As will be described in detail hereinafter, an automated image-guided therapy system and method in accordance with exemplary aspects of the present technique are presented. Based on image data acquired by the image-guided therapy system via an imaging and therapy catheter, a user may assess need for therapy in an anatomical region and use a human interface device, such as a mouse, to direct the therapy via the image-guided therapy system.

Figure 1:
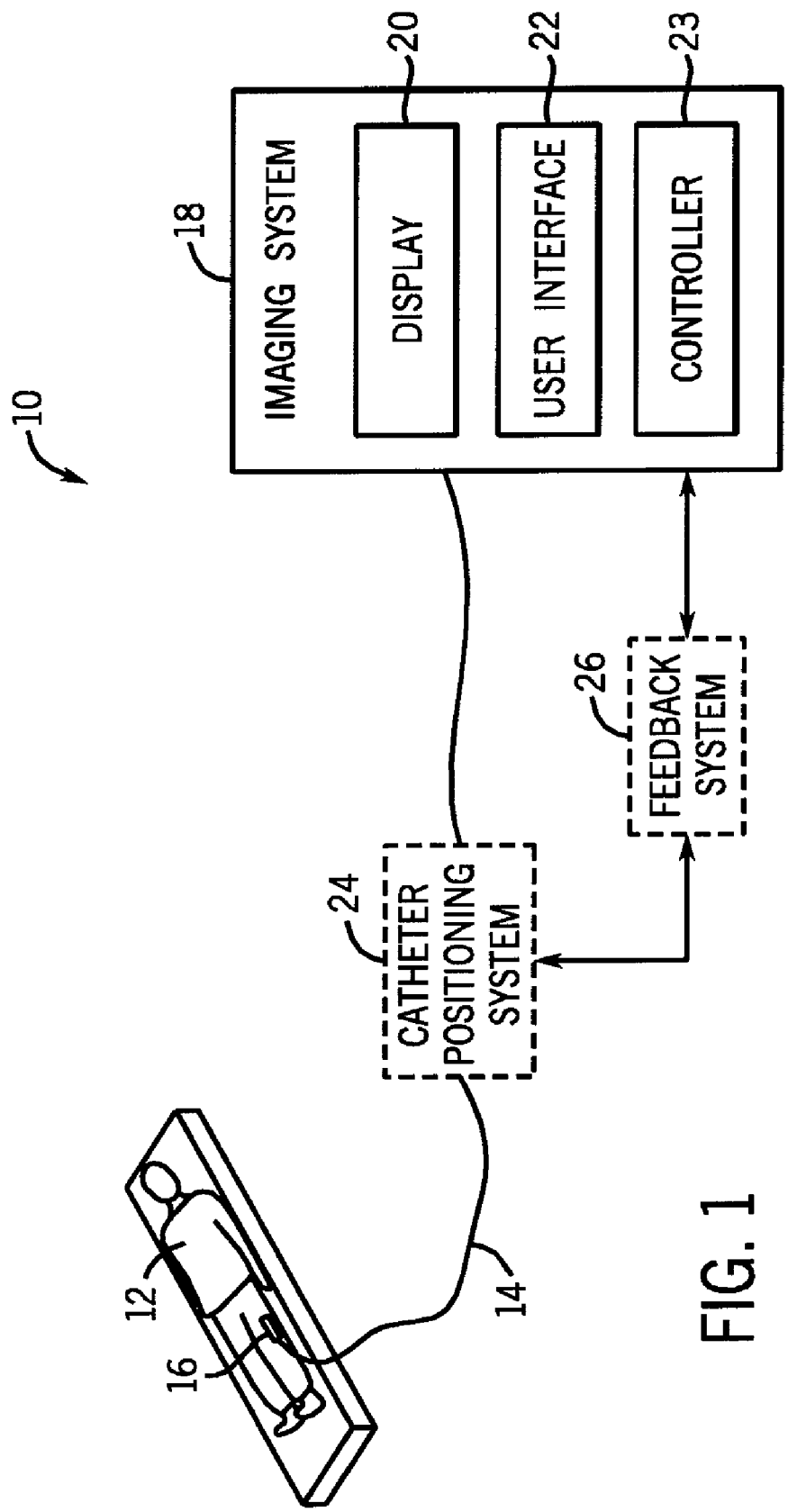
FIG. 1 is a block diagram of an exemplary ultrasound imaging and therapy system in accordance with aspects of the present invention.

FIG. 1 is a block diagram of an exemplary system 10 for use in imaging and providing therapy to one or more regions of interest in accordance with aspects of the present technique. The system 10 may be configured to acquire image data from a patient 12 via an imaging and therapy catheter 14. As used herein, "catheter" is broadly used to include conventional catheters, transducers or devices adapted for applying therapy. Further, as used herein, "imaging" is broadly used to include two-dimensional imaging, three-dimensional imaging, or preferably, real-time three-dimensional imaging. Reference numeral 16 is representative of a portion of the imaging and therapy catheter 14 disposed inside the vasculature of the patient 12.

In certain embodiments, an imaging orientation of the imaging and therapy catheter 14 may include a forward viewing catheter or a side viewing catheter. However, a combination of forward viewing and side viewing catheters may also be employed as the imaging and therapy catheter 14. The imaging and therapy catheter 14 may include a real-time imaging and therapy transducer (not shown). According to aspects of the present technique, the imaging and therapy transducer may include integrated imaging and therapy components. Alternatively, the imaging and therapy transducer may include separate imaging and therapy components. The imaging and therapy transducer will be described in greater detail with reference to FIGS. 3-4 and 6-18. It should be noted that although the embodiments illustrated are described in the context of a catheter-based transducer, other types of transducers such as transesophageal transducers, transthoracic transducers laparoscopic transducers, or intraoperative transducers are also contemplated.

In accordance with aspects of the present technique, the imaging and therapy catheter 14 may be configured to image an anatomical region to facilitate assessing need for therapy in one or more regions of interest within the anatomical region of the patient 12 being imaged. Additionally, the imaging and therapy catheter 14 may also be configured to deliver therapy to the identified one or more regions of interest. As used herein, "therapy" is representative of ablation, hyperthermia, percutaneous ethanol injection (PEI), cryotherapy, ultrasound-enhanced or thermally-enhanced drug delivery and laser-induced thermotherapy. Additionally, "therapy" may also include delivery of tools, such as needles for delivering gene therapy, for example. Additionally, as used herein, "delivering" may include various means of providing therapy to the one or more regions of interest, such as conveying therapy to the one or more regions of interest or directing therapy towards the one or more regions of interest. As will be appreciated, in certain embodiments the delivery of therapy, such as RF ablation, may necessitate physical contact with the one or more regions of interest requiring therapy. However, in certain other embodiments, the delivery of therapy, such as high intensity focused ultrasound (HIFU) energy, may not require physical contact with the one or more regions of interest requiring therapy.

The system 10 may also include a medical imaging system 18 that is in operative association with the imaging and therapy catheter 14 and configured to define a therapy pathway to facilitate delivering therapy to the one or more regions of interest. The imaging system 10 may be configured to define the therapy pathway in response to user input or automatically define the therapy pathway as will be described in greater detail with reference to FIG. 5. Accordingly, in one embodiment, the medical imaging system 18 may be configured to provide control signals to the imaging and therapy catheter 14 to excite the therapy component of the imaging and therapy transducer and deliver therapy to the one or more regions of interest. In addition, the medical imaging system 18 may be configured to acquire image data representative of the anatomical region of the patient 12 via the imaging and therapy catheter 14. Medical imaging system 18 further includes a system controller 23 that controls operation of the system, and its components.

As illustrated in FIG. 1, the imaging system 18 may include a display area 20 and a user interface area 22. However, in certain embodiments, such as in a touch screen, the display area 20 and the user interface area 22 may overlap. Also, in some embodiments, the display area 20 and the user interface area 22 may include a common area. In accordance with aspects of the present technique, the display area 20 of the medical imaging system 18 may be configured to display an image generated by the medical imaging system 18 based on the image data acquired via the imaging and therapy catheter 14. Additionally, the display area 20 may be configured to aid the user in defining and visualizing a user-defined therapy pathway as will be described in greater detail hereinafter. It should be noted that the display area 20 may include a three-dimensional display area. In one embodiment, the three-dimensional display may be configured to aid in identifying and visualizing three-dimensional shapes.

Further, the user interface area 22 of the medical imaging system 18 may include a human interface device (not shown) configured to facilitate the user in identifying the one or more regions of interest for delivering therapy using the image of the anatomical region displayed on the display area 20. The human interface device may include a mouse-type device, a trackball, a joystick, a stylus, or a touch screen configured to facilitate the user to identify the one or more regions of interest requiring therapy and define a suitable therapy pathway on the image being displayed on the display area 20. For example, the human interface device responds to a user-defined pathway by displaying a line, for instance, and will be described in greater detail with reference to FIG. 2. Additionally, the human interface device may be configured to facilitate delivery of therapy to the identified one or more regions of interest. However, as will be appreciated, other human interface devices, such as, but not limited to, a touch screen, may also be employed.

It may be noted that although the exemplary embodiments illustrated hereinafter are described in the context of an ultrasound system, other medical imaging systems such as, but not limited to, optical imaging systems, or electro-anatomical imaging systems are also contemplated for defining a therapy pathway to facilitate delivering therapy to the one or more regions of interest.

As depicted in FIG. 1, the system 10 may include an optional catheter positioning system 24 configured to reposition the imaging and therapy catheter 14 within the patient 12 in response to input from the user and relative to the defined therapy pathway. The catheter positioning system 24 will be described in greater detail hereinafter. Moreover, the system 10 may also include an optional feedback system 26 that is in operative association with the catheter positioning system 24 and the medical imaging system 18. The feedback system 26 may be configured to facilitate communication between the catheter positioning system 24 and the medical imaging system 18, as will be discussed in greater detail hereinafter.

Figure 2:
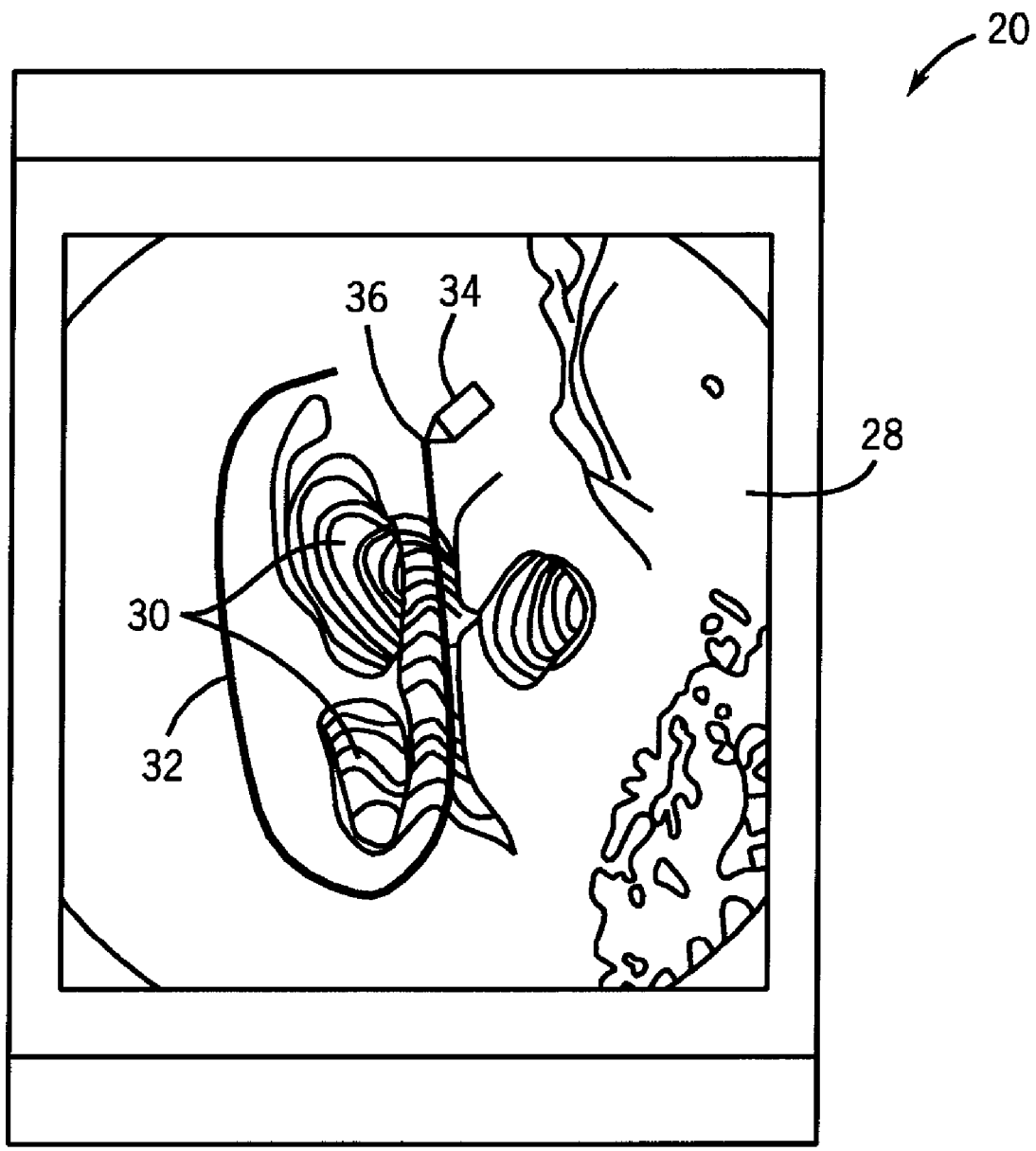
FIG. 2 is a front view of a display area of the imaging and therapy system of FIG. 1 in accordance with aspects of the present invention.

Turning now to FIG. 2, a front view of the display area 20 of the medical imaging system 18 of FIG. 1 is illustrated. Reference numeral 28 is representative of an image generated by the medical imaging system 18 (see FIG. 1) based on the image data acquired via the imaging and therapy catheter 14 (see FIG. 1) from an anatomical region of the patient 12 (see FIG. 1). Further, reference numeral 30 embodies one or more regions of interest requiring therapy identified by the user employing the displayed image 28. The user may define a therapy pathway 32 on the image 28 to select the one or more regions of interest requiring therapy. As previously noted, the user may define the therapy pathway 32 on the image 28 via a human interface device 34 such as a stylus, a trackball, a mouse, a touch screen, or a joystick, for example. In the illustrated embodiment, the human interface device is shown as including a stylus 34. It should be noted that a currently selected region of interest 36 is depicted by the current position of the stylus 34.

Figure 3:
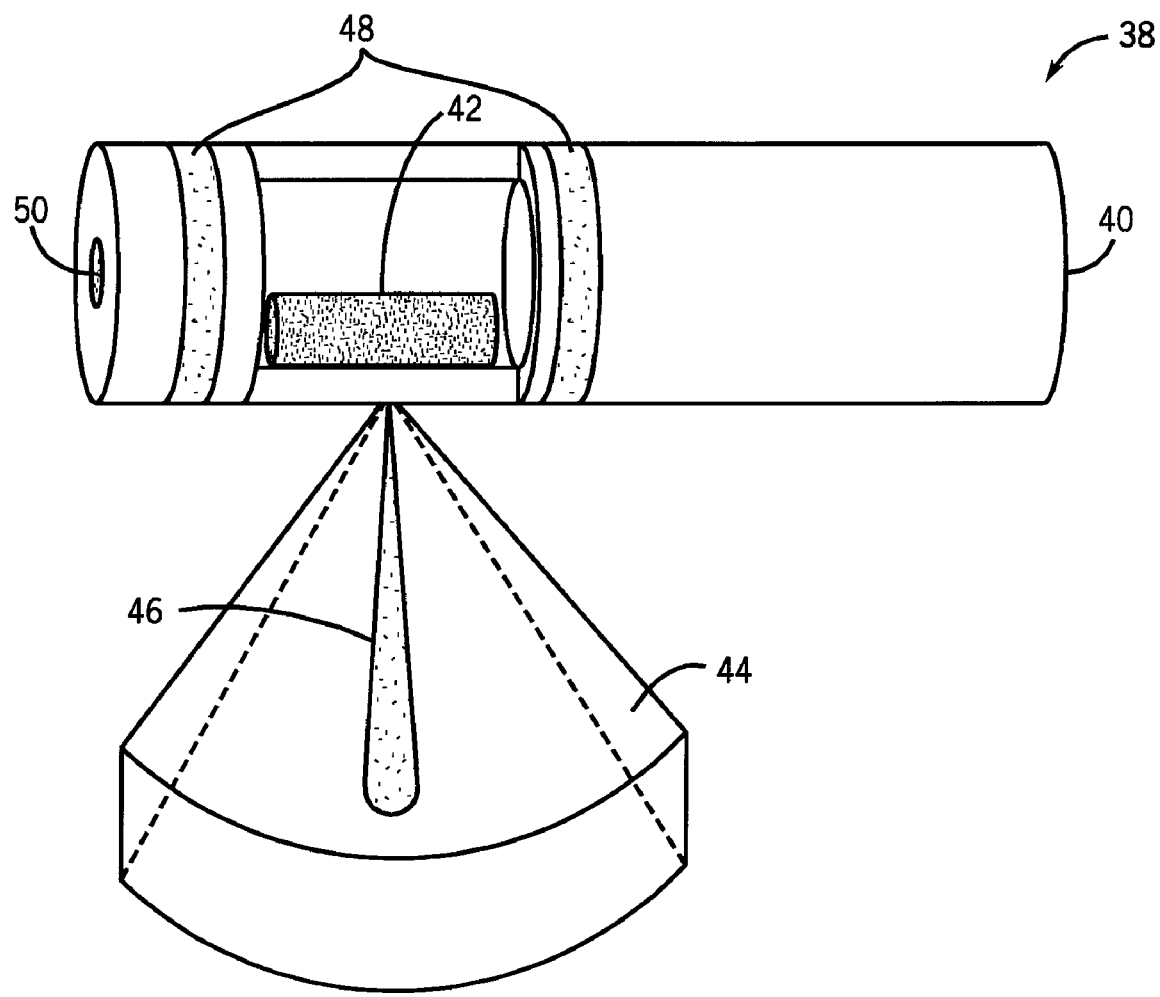
FIG. 3 is an illustration of an exemplary imaging and therapy transducer for use in the system illustrated in FIG. 1 in accordance with aspects of the present invention.

FIG. 3 is an illustration of an exemplary embodiment 38 of an imaging and therapy catheter 40 for use in the system 10 illustrated in FIG. 1. Further, in FIG. 3, the imaging and therapy catheter 40 is illustrated as having an imaging and therapy transducer 42. As previously noted, the imaging and therapy catheter 40 may include an imaging and therapy transducer having integrated or separate imaging and therapy components. The embodiment of the imaging and therapy catheter 40 illustrated in FIG. 3 is shown as having an integrated imaging and therapy transducer 42 having integrated imaging and therapy components. In one embodiment, the illustrated integrated imaging and therapy catheter 40 may be configured to facilitate real-time three-dimensional imaging of an anatomical region as well as deliver therapy to one or more regions in the anatomical region. For example, in the case of an integrated ultrasound imaging and therapy catheter, a real-time, three-dimensional ultrasound image may be obtained using a two-dimensional array or mechanically scanning one-dimensional array as the imaging component of the imaging and therapy transducer 42. Additionally, the integrated ultrasound imaging and therapy catheter 40 may also be configured to deliver therapy in the form of ultrasound ablation energy via a therapy component of the imaging and therapy transducer 42.

Further, reference numeral 44 is representative of a real-time three-dimensional imaged volume (RT3D). In the illustrated embodiment, the real-time three-dimensional imaged volume 44 is shown as having a pyramidal volume. In a presently contemplated configuration, reference numeral 46 is representative of a steerable beam capable of providing therapy to the identified one or more regions of interest (not shown). It should be noted that the ablation beam 46 may be steered manually or electronically. The ablation beam 46 may be steered within the three-dimensional imaged volume 44. Alternatively, the ablation beam 46 may include an ablation beam positioned in a fixed location with respect to the imaging and therapy catheter 40. The imaging and therapy catheter 40 illustrated in FIG. 3 may also include electrodes 48. The electrodes 48 may be configured to capture cardiac electrical waveforms to monitor electrical activity of the heart, for example. Additionally, in certain embodiments, the imaging and therapy catheter 40 may include a position sensor 50 disposed in or near a tip of the imaging and therapy catheter 40. The position sensor 50 may be configured to track motion of the imaging and therapy catheter 40 within the anatomy of the patient. Subsequently, the medical imaging system 18 (see FIG. 1) may be configured to acquire location information from the position sensor 50.

Figure 4:
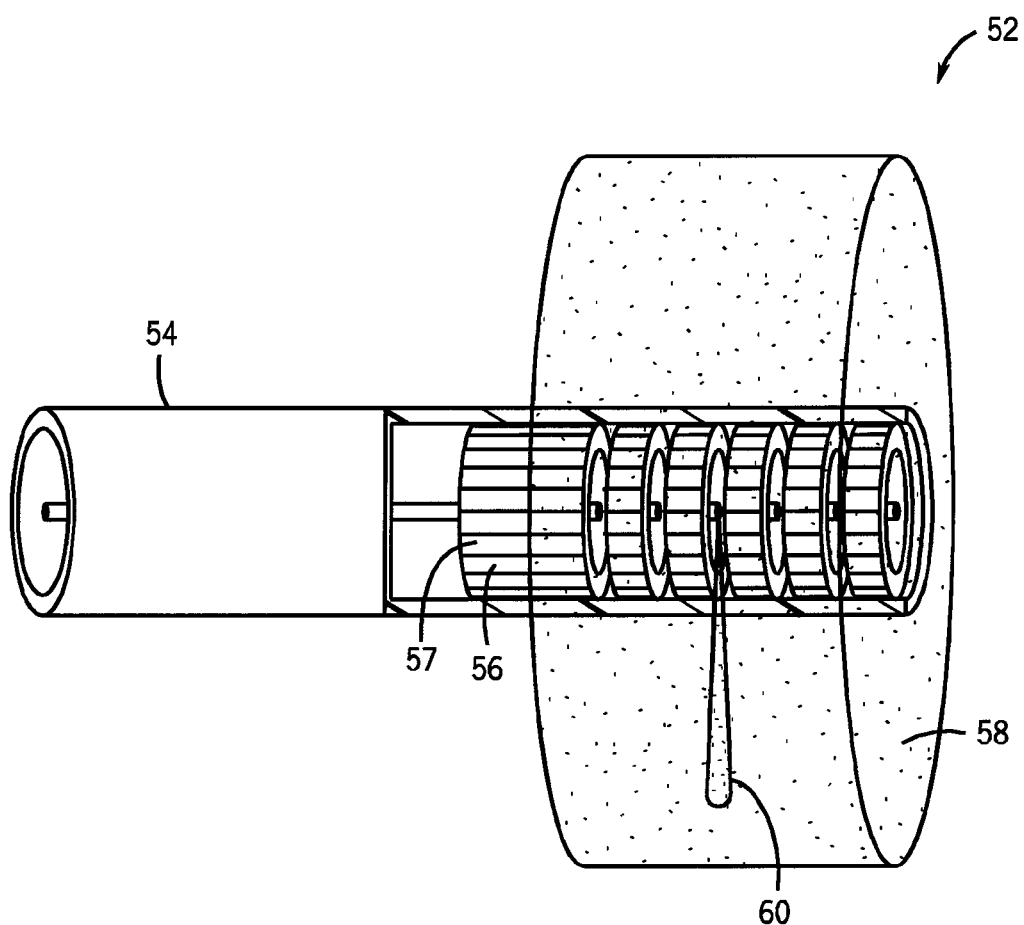
FIG. 4 is an illustration of another exemplary imaging and therapy transducer for use in the system illustrated in FIG. 1 in accordance with aspects of the present invention.

Referring now to FIG. 4, an exemplary embodiment 52 of an imaging and therapy catheter 54 having a large field of view is illustrated. The large field of view may encompass 360 degrees, in one embodiment. As depicted in FIG. 4, the imaging and therapy catheter 54 is illustrated as having an imaging and therapy transducer 56. In certain embodiments, the imaging and therapy catheter 54 may include a single imaging and therapy transducer having a large field of view. Alternatively, in other embodiments, a plurality of imaging and therapy transducers may be used in the imaging and therapy catheter 54. Further, reference numeral 58 is representative of a real-time three-dimensional imaged volume. In the illustrated embodiment, the real-time three-dimensional imaged volume 58 is shown as having a cylindrical volume. The imaging beam is mechanically and/or electronically scanned throughout the imaged volume 58. In a presently contemplated configuration, reference numeral 60 is representative of a steerable beam capable of providing therapy to the identified one or more regions of interest (not shown). The ablation beam 60 may be steered within the three-dimensional imaged volume 58. Also, as previously noted, the ablation beam 60 may be steered manually or electronically. Alternatively, the ablation beam 60 may include an ablation beam positioned in a fixed location with respect to the imaging and therapy catheter 54. As further shown in FIG. 4, it is contemplated that the ultrasound transducer may comprise a number of transducer sub-elements 57 that, as will be described, may be independently and selectively activated.

Although the embodiments illustrated in FIGS. 3 and 4 are described in the context of ultrasound ablation, it should be noted that other methods of ablation may also be employed. For instance, RF ablation may be used. Accordingly, the user may identify locations of the one or more regions of interest requiring therapy on the displayed image 28 (see FIG. 2). The medical imaging system 18 (see FIG. 1) may then be configured to control the positioning system 24 to guide the imaging and therapy catheter to the desired locations and deliver ablation energy.

Figure 5:
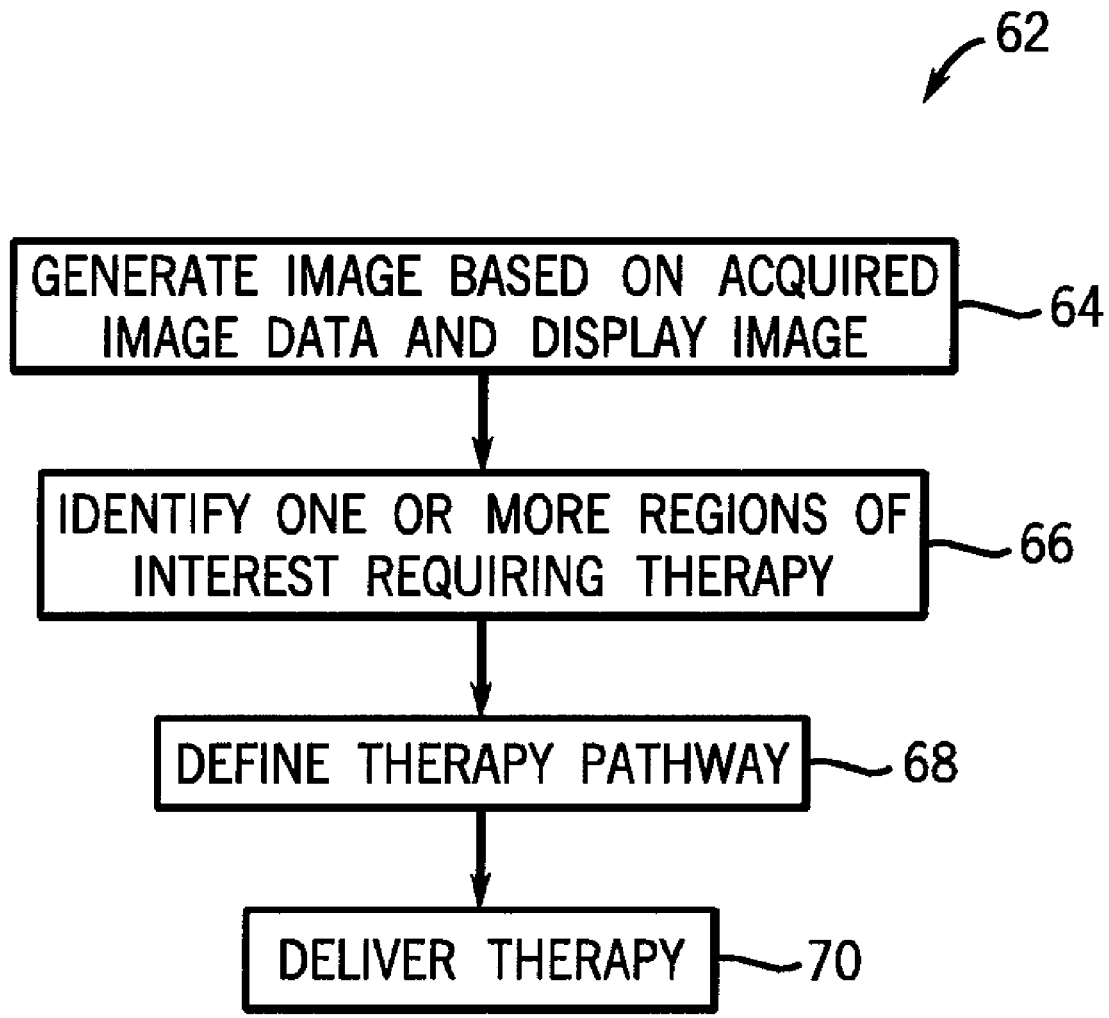
FIG. 5 is a flow chart illustrating an exemplary process of imaging and providing therapy to one or more regions of interest in accordance with aspects of the present invention.

FIG. 5 is a flow chart of exemplary logic 62 for imaging and providing therapy to one or more regions of interest. In accordance with exemplary aspects of the present technique, a method for imaging and providing therapy to the one or more regions of interest is presented. The method starts at step 64 where an image based on image data acquired by the medical imaging system 18 (see FIG. 1) is generated. As previously noted, the image data representative of an anatomical region of the patient 12 (see FIG. 1) may be acquired via an imaging and therapy catheter, such as imaging and therapy catheters 40 and 54 illustrated in FIG. 3 and FIG. 4 respectively. The image data may be acquired in real-time employing the imaging and therapy catheter. This acquisition of image data via the imaging and therapy catheter aids a user in assessing need for therapy in the anatomical region being imaged. In addition, mechanical means, electronic means or combinations thereof may be employed to facilitate the acquisition of image data via the imaging and therapy catheter. Alternatively, previously stored image data representative of the anatomical region may be acquired by the medical imaging system 18. The imaging and therapy catheter may include an imaging and therapy transducer. Further, an imaging orientation of the imaging and therapy catheter may include a forward viewing catheter, a side viewing catheter or combinations thereof, as previously described.

Also, the generated image, such as image 28 (see FIG. 2) is displayed on the display area 20 (see FIG. 1) of the medical imaging system 18 at step 64. In certain embodiments, the displayed image may include a real-time three-dimensional imaged volume.

Subsequently, at step 66, one or more regions of interest requiring therapy may be identified on the displayed image. In certain embodiments, the user may visually identify the one or more regions of interest using the displayed image. Alternatively, in accordance with aspects of the present technique, tissue elasticity or strain imaging techniques may be employed to aid the user in assessing the need for therapy in the one or more regions of interest. The tissue elasticity imaging techniques may include acoustic radiation force impulse (ARFI) imaging or vibroacoustography, for example. Strain imaging techniques may include strain imaging, strain rate imaging, tissue velocity imaging, or tissue synchronization imaging. The imaging and therapy transducer may be used to facilitate elasticity or strain imaging. However, a separate dedicated array that is integrated onto the imaging and therapy catheter may be utilized to achieve elasticity or strain imaging.

Following step 66, the user may define a therapy pathway, such as the therapy pathway 32 (see FIG. 2) on the displayed image at step 68. The therapy pathway is defined in response to the identified one or more regions of interest. Accordingly, in one embodiment, the therapy pathway may extend beyond a region that is capable of being imaged and treated from a single catheter position, thus requiring multiple catheter positions. Image data representative of a larger field of view may be acquired and stored. This process of acquiring and storing of image data embodying the larger field of view will be described in greater detail hereinafter. As previously noted, the user may utilize a mouse-type input device located on the user interface area 22 (see FIG. 1) of the medical imaging system 18 to draw the therapy pathway. Alternatively, the user may use a stylus, a joystick, a trackball device or a touch screen to draw the therapy pathway. The medical imaging system 18 then records the therapy pathway and displays the therapy pathway on the displayed image by overlaying the defined therapy pathway on the displayed image. The overlaying of the therapy pathway on the displayed image allows the user to visualize the therapy pathway in real-time.

It should be noted that although the embodiments illustrated are described in the context of a user-defined therapy pathway, where the user manually delineates the therapy pathway, an automatically defined therapy pathway is also contemplated. The imaging and therapy system 10 (see FIG. 1) may be configured to provide a system-generated proposed therapy pathway based on selected characteristics of the image data. Accordingly, the system 10 may be configured to automatically identify one or more regions in the imaged volume requiring therapy based on the selected characteristics. Subsequently, the system 10 may also automatically propose a therapy pathway based on locations of the identified one or more regions requiring therapy. The selected characteristics may include mechanical properties of tissues, such as, but not limited to, density, brightness, or tissue stiffness, or may include blood flow properties in the tissue, such as blood velocity, perfusion, or doppler power, or any combinations thereof which may be indicative or representative of certain diseases or anatomy that would respond to therapy.

Step 70 depicts a process of delivering therapy to the identified one or more regions of interest in accordance with the defined pathway. During step 70, the medical imaging system 18 processes the therapy pathway defined at step 68 and converts the defined therapy pathway into a series of actions resulting in execution of the therapy in accordance with the therapy pathway defined in step 68. The series of actions resulting in execution of the therapy depend on the specific embodiment and will be described in greater detail hereinafter. Accordingly, the medical imaging system 18 is configured to determine location information of each of the one or more regions of interest. The medical imaging system 18 may be configured to determine location information of each of the one or more regions of interest by processing the defined therapy pathway in combination with known location information of each point on the displayed image relative to the known positions of the imaging and therapy components of the catheter.

With continuing reference to step 70, if the one or more regions of interest are located within the field of view of the imaging and therapy transducer, the medical imaging system 18 may be configured to deliver therapy through the therapy component of the imaging and therapy transducer in the imaging and therapy catheter to the identified one or more regions of interest. In one embodiment, the therapy may include high intensity focused ultrasound (HIFU) energy. The medical imaging system may deliver the therapy by steering an ablation beam, such as ablation beams 46 (see FIG. 3) and 60 (see FIG. 4) within the imaged volume. Accordingly, in one embodiment, the ablation beam may include a steerable ablation beam. The ablation beam may be steered using conventional phasing techniques that include phasing excitation of the ablation array to ensure propagation of the ultrasound beam in a desirable direction. It should be noted if the ablation beam is steerable, the one or more regions of interest within the field of view of the imaging and therapy transducer may be ablated without repositioning the imaging and therapy catheter, thereby advantageously resulting in less movement of the imaging and therapy catheter within the patient. Also, if the imaging and therapy transducer has a large field of view, such as the imaging and therapy catheter 54 illustrated in FIG. 4, the one or more regions of interest may be ablated while the imaging and therapy catheter is positioned at a single location.

Alternatively, if the ablation beam is fixed, the imaging and therapy catheter may need to be repositioned prior to delivering therapy. A check may then be carried out at an optional step to verify if the one or more regions of interest requiring therapy are positioned within a field of view of the imaging and therapy transducer. If the one or more regions of interest requiring therapy are currently positioned outside the field of view of the imaging and therapy transducer, then the imaging and therapy catheter may be repositioned to include the one or more regions of interest within the field of view of the imaging and therapy transducer. This repositioning of the imaging and therapy catheter facilitates imaging and delivering therapy to the one or more regions of interest that are currently located outside the field of view of the imaging and therapy catheter. Additionally, if the one or more regions of interest requiring therapy includes a three-dimensional shape, repositioning of the imaging and therapy catheter may be required to cover the three-dimensional shape.

Furthermore, in accordance with aspects of the present technique, three-dimensional volumes with a larger field of view may be assembled by employing an imaging and therapy catheter having a limited field of view. Moreover, information regarding the three-dimensional volumes and defined therapy pathways may be stored in memory, for example. Consequently, a composite image may be generated by assembling several images, where the images are representative of a plurality of positions of the imaging and therapy catheter. The composite image may be stored in memory. This assembly of three-dimensional volumes with a larger field of view may be achieved by tracking image characteristics, such as speckle targets, or other image features. The current field of view imaged by the imaging and therapy catheter may then be registered with the larger stored three-dimensional volume in real-time. This allows a user to identify where the localized treatment pathway is located with respect to an overall treatment pathway when the overall treatment pathway extends beyond what is visible at a single given instant. In one embodiment, one or more regions of interest selected by the user may be located outside a field of view of the current position of the imaging and therapy catheter. The imaging and therapy catheter may then be accordingly repositioned to include within the current field of view the one or more regions of interest presently located outside the field of view of the imaging and therapy catheter, while moving the treated one or more regions of interest out of the field of view.

In one embodiment, the imaging and therapy catheter may include a position sensor 50 (see FIG. 3) disposed in or near a tip of the imaging and therapy catheter. As previously noted, the position sensor 50 may be configured to track motion of the imaging and therapy catheter within the anatomy of the patient. Subsequently, the medical imaging system may be configured to acquire location information from the position sensor.

In certain embodiments, the imaging and therapy catheter may be repositioned manually. Alternatively, the imaging and therapy catheter may be automatically repositioned to image and deliver therapy to the one or more regions of interest employing the catheter positioning system 24 illustrated in FIG. 1. The catheter positioning system 24 may include a sub-system (not shown) that may be configured to provide location information regarding a tip of the imaging and therapy catheter. As used herein, "tip" of the imaging and therapy catheter is representative of a length of about 10 centimeters or less from a distal end of the imaging and therapy catheter. In certain embodiments, the tip of the imaging and therapy catheter also may include the imaging and therapy components of the imaging and therapy catheter.

Further, the catheter positioning system 24 may also include an actuating sub-system (not shown) that may be configured to actuate the tip of the catheter. Accordingly, the location information associated with the one or more regions of interest currently located outside the field of view of the imaging and therapy catheter may be communicated to the catheter positioning system 24 via the feedback system 26 (see FIG. 1). The user may utilize the human interface device to provide information regarding location of a subsequent volume to be imaged to the catheter positioning system 24 via the feedback system 26, for example. Consequently, the catheter positioning system 24 may be configured to automatically reposition the imaging and therapy catheter to the desirable location thereby ensuring that the one or more regions of interest are positioned within the field of view of the imaging and therapy catheter.

It should also be noted that the process of delivering therapy may be preferably performed in real-time. Accordingly, the imaging and therapy catheter may deliver therapy in real-time to the one or more regions of interest in response to input from the user. In other words, therapy may be delivered to the one or more regions of interest while the user is drawing the therapy pathway on the displayed image. In view of this, the medical imaging system may be configured to track the defined therapy pathway as it is drawn on the displayed image. Subsequently, the imaging and therapy catheter may be configured to steer the ablation beam to deliver the therapy. Alternatively, the medical imaging system may be configured to deliver the therapy to the one or more regions of interest after the therapy pathway has been drawn to a predetermined extent.

Additionally, the efficacy of the therapy after it is delivered may be monitored via the use of the tissue elasticity or strain imaging techniques. Also, the medical imaging system may be configured to use imaging processing algorithms to accurately monitor the therapy treated sites. The imaging processing algorithms may also be used to monitor motion of the tissue being imaged and treated. In certain embodiments, the image processing algorithms may include speckle tracking algorithms or other correlation-based algorithms.

It should also be noted that the procedure of imaging and providing therapy to the one or more regions of interest requiring therapy may be executed from a remote location once the imaging and therapy catheter has been positioned within the patient. The user may access the image data from a remote location, which may advantageously assist the user in remotely monitoring the delivery of therapy. The image data acquired via the imaging and therapy catheter may be transmitted via a wired or a wireless medium to a central monitoring system that may be located within a caregiving facility. The user may then access the central monitoring system to remotely view the image data, identify the one or more regions requiring therapy, and deliver the therapy accordingly. In general, displays, printers, workstations, and similar devices supplied within the system may be local to the image acquisition components, or may be remote from these components, such as elsewhere within caregiving facility, or in an entirely different location, linked to the medical imaging system via one or more configurable networks, such as the Internet, virtual private networks, and so forth.

As will be appreciated by those of ordinary skill in the art, the foregoing example, demonstrations, and process steps may be implemented by suitable code on a processor-based system, such as a general-purpose or special-purpose computer. It should also be noted that different implementations of the present technique may perform some or all of the steps described herein in different orders or substantially concurrently, that is, in parallel. Furthermore, the functions may be implemented in a variety of programming languages, such as C++ or Java. Such code, as will be appreciated by those of ordinary skill in the art, may be stored or adapted for storage on one or more tangible, machine readable media, such as on memory chips, local or remote hard disks, optical disks (that is, CD's or DVD's), or other media, which may be accessed by a processor-based system to execute the stored code. Note that the tangible media may comprise paper or another suitable medium upon which the instructions are printed. For instance, the instructions can be electronically captured via optical scanning of the paper or other medium, then compiled, interpreted or otherwise processed in a suitable manner if necessary, and then stored in a computer memory.

The present invention is also directed to an integrated imaging and ablation catheter that may be used with the integrated imaging and therapy system heretofore described. As will become readily apparent, the invention advantageously improves registration of the imaging plane with an ablation target which aids in the precise placement of ablation lesions on targeted anatomy. Moreover, the invention improves the ability for an operator to visualize ablation reticles on an image prior to ablation. The invention further provides flexibility to an operator in performing a given ablation. That is, it is contemplated that an ablation beam may be steered to an operator specified site without requiring operator repositioning of the catheter. Thus, the invention supports ablation beam steering with a relatively static catheter.

It will also be shown that the present invention supports contact-less ablation. That is, through improved visualization, the present invention avoids the conventional need to physically contact the ablation point or tissue with the catheter when identifying an ablation location. In one exemplary embodiment, the integrated ablation and imaging catheter has independently controllable ablation array elements that may be excited with different frequencies, phases, time delays, or amplitudes to enable multiple ablation sites to be ablated simultaneously. The present invention also allows for the automatic assessment of ablation efficiency using strain rate imaging or ARFI, and automatic reapplication of ablation energy if necessary.

It is also contemplated that the integrated ablation and imaging arrays may be fabricated together thereby reducing fabrication costs and time. It is also contemplated that real-time 3D imaging may be integrally or simultaneously performed during an ablation procedure.

Referring now to FIG. 6, an exemplary integrated ultrasound imaging and ablation catheter or probe is shown. Catheter 72 includes a catheter body 74 that houses an ablation array 76 and an imaging array 78. The ablation array 76 is formed by a plurality of ablation elements 80 and the imaging array comprises a plurality of transducer elements 82. The ablation array and imaging array are controlled by control commands that are input thereto across interconnect leads 84. In addition to providing control commands, the interconnect leads 84 include readout leads that carry imaging data from the imaging array elements to the imaging system (FIG. 1). As shown in the exemplary embodiment of FIG. 6, the ablation array and the imaging array, while commonly housed within the catheter body, are separate and distinguishable arrays; however, both arrays extend along the long axis of the catheter body which provides a large aperture that is preferred for effective ablation. A skilled artisan will appreciate that the ablation array may be used to steer the ultrasonic ablation beam as permitted by the frequency and geometry of the ablation array.

Referring now to FIG. 7, the operating frequencies of the ablation and imaging arrays may be distinct from one another. As shown, the frequency response of the ablation array 86 does not overlap the frequency response of the imaging array 88. As will be described further, this non-overlapping of the frequency responses can be exploited to achieve simultaneous imaging and ablation. However, as shown in FIG. 8, it is contemplated that the frequency responses could overlap. And thus, imaging frames may be interleaved with ablation beams.

As shown in FIG. 9, it is contemplated that the ablation and imaging arrays may be separate arrays housed within a single catheter body. Notwithstanding the separation between the arrays 76, 78, the imaging array is constructed to provide an imaging region 90 that includes the ablation beam 92 of the ablation array 76. As shown in FIG. 10, is also contemplated that the ablation and imaging arrays 76, 78 are constructed in a common array 94. In either construction, the imaging region 90 of the imaging array 78 is sufficiently large to encompass the ablation target 96 and, thus, the ablation target is inherently aligned in the image plane (imaged region).

Figure 11:
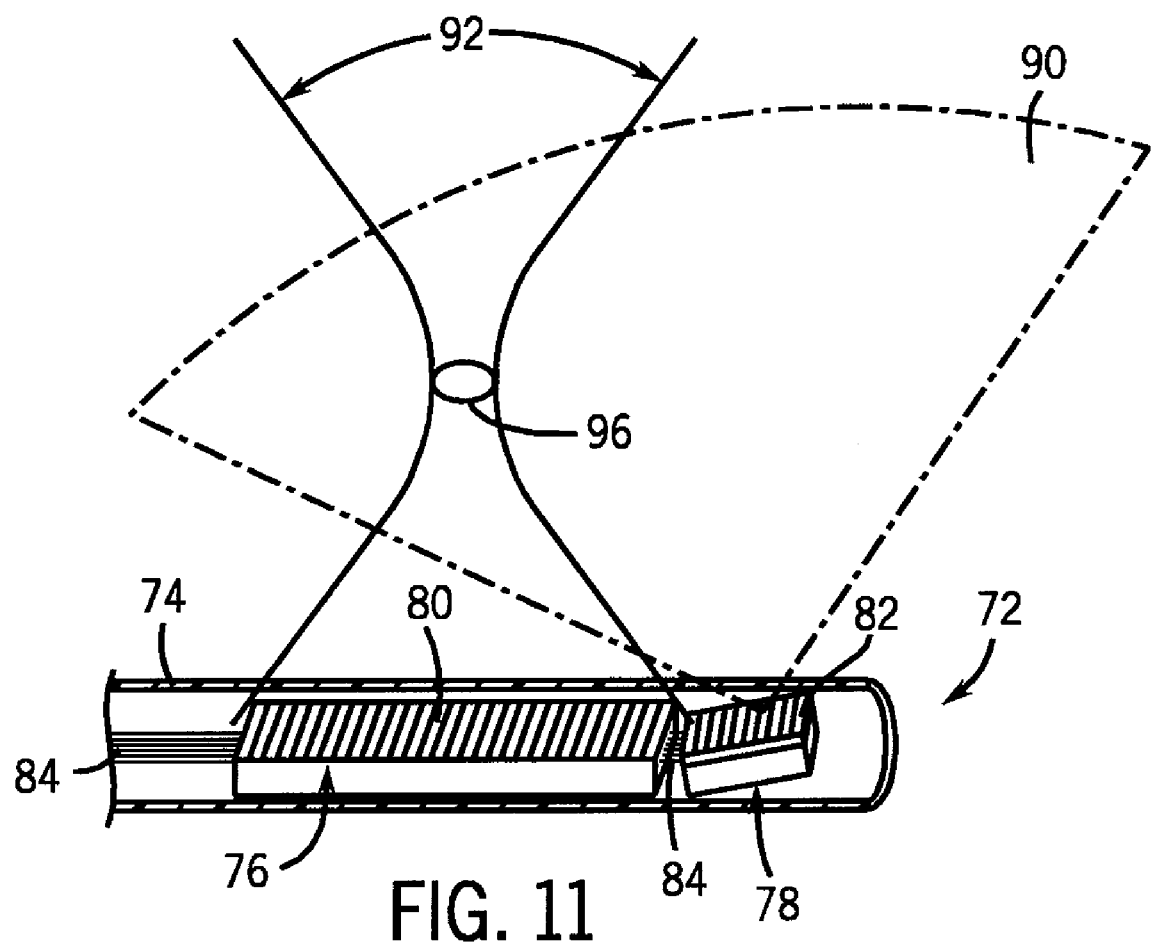
FIG. 11 illustrates another exemplary catheter in accordance with aspects of the present invention wherein the imaging array is tilted relative to the therapy array.

Referring now to FIG. 11, another exemplary embodiment of an integrated ablation and imaging catheter is shown. In this embodiment, the ablation and imaging arrays are tilted relative to one another to improve centering of the ablation beam in the imaged region. In the illustrated example, the imaging array 78 is shown in a tilted position relative to the ablation array 76. However, it is contemplated that the ablation array could be tilted relative to the imaging array. By tilting the imaging array 78, the imaged region 90 of the imaging array 78 is also tilted relative to the ablation beam 92 of the ablation array 76. A skilled artisan will appreciate that the degree of tilt of the imaging array will define the angular offset of the imaged region. In a preferred embodiment, the imaging array is constructed to be tilted in the range of zero to ninety degrees relative to the ablation array.

It is contemplated that one or more of a number of actuating devices may be used to tilt the imaging array and/or ablation array. For example, the arrays could be titled by bending the flexible interconnect circuit to which the arrays are connected and then setting or pointing the arrays to a desired tilted position. In another contemplated embodiment, a mechanical pull wire connected to the arrays and extending through the catheter may be used by a technician to tilt the arrays. On the other hand, an electromechanical actuator (not shown) may be connected to the pull wire or the arrays directly to effectuate desired tilting motion. It is also possible for a hydraulic circuit to be used to tilt the arrays based on the forcing in or extracting out fluid from a balloon or bladder. It is contemplated that other devices may be used to tilt the arrays.

Figure 12:
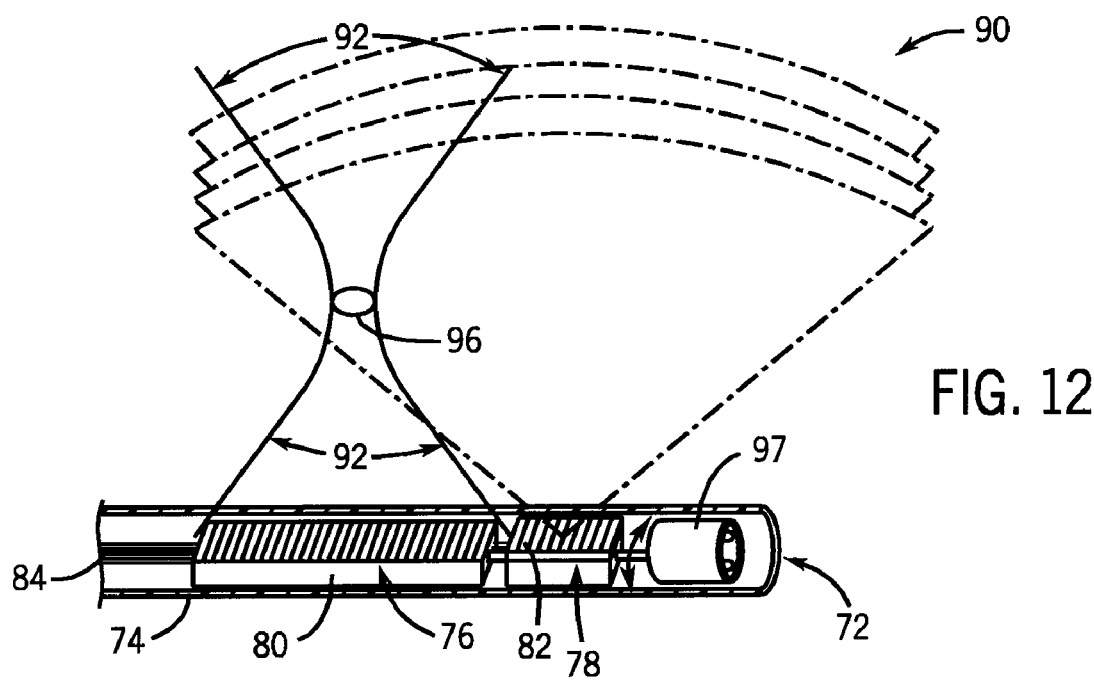
FIG. 12 illustrates a 4D mechanically scanning probe with an integrated therapy array in accordance with another embodiment of the invention.
Figure 13:
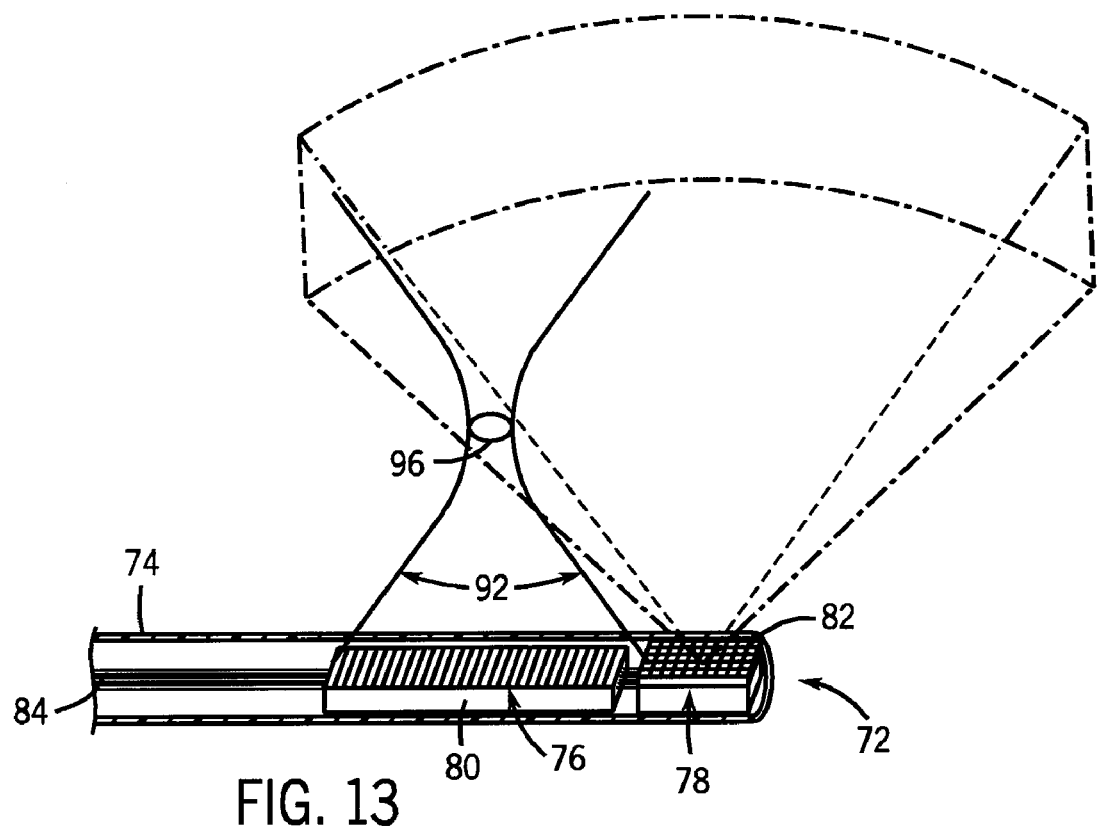
FIG. 13 illustrates a 4D electronically scanning probe with an integrated therapy array in accordance with another embodiment of the present invention.

It is also contemplated that either the ablation array or the imaging array or both may be a real-time 3D (4D) array. Two exemplary embodiments are illustrated in FIGS. 12-13. FIG. 12 illustrates a 1D mechanically scanning imaging array with an integrated 1D ablation array. It is contemplated that the motor 97 could rotate the ablation array, the imaging array, or both. In the embodiment where both the 1D imaging and 1D ablation arrays are rotated, real-time 3D imaging and real-time 3D ablation are possible without moving the catheter. FIG. 13 illustrates a 2D electronically scanning imaging array with an integrated 1D ablation array. Such a configuration allows real-time 3D imaging and ablation in two dimensions along a single plane internal to the 3D imaged volume. It is also contemplated that the integrated array may be a 2D imaging and 2D ablation array (not shown). Such a construction would also allow for full real-time 3D imaging and real-time 3D ablation without requiring catheter motion.

Figure 14:
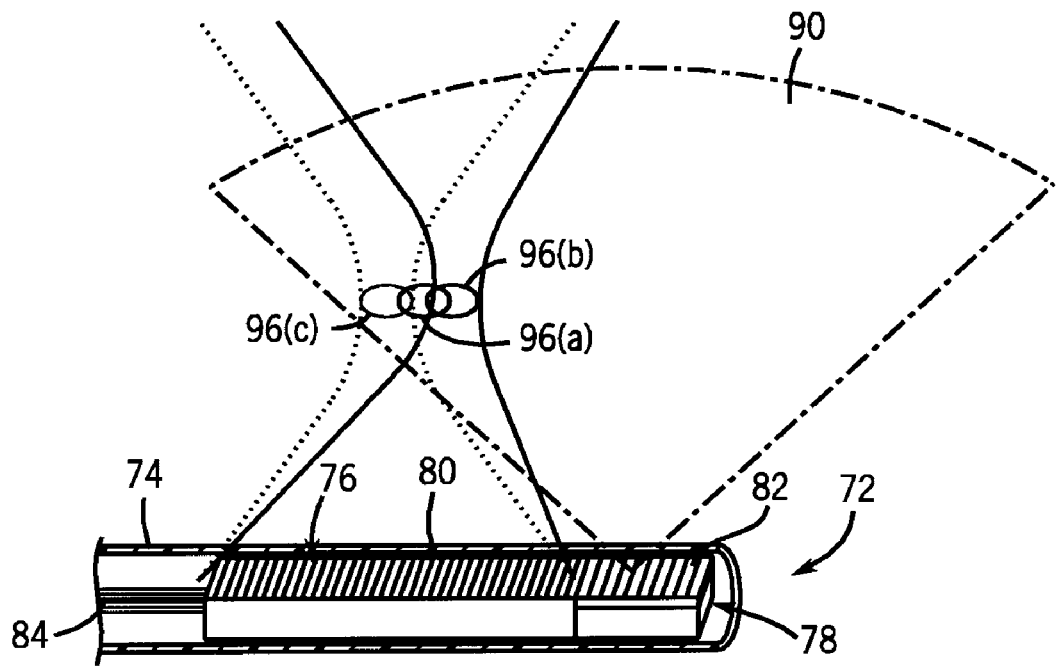
FIG. 14 illustrates ablation of multiple therapy points from a single catheter position in accordance with further aspects of the present invention.

As shown in FIG. 14, electronic steering of the ablation beam allows multiple ablation sites 96(a), 96(b), and 96(c) to be ablated at a single catheter position. Not only does this reduce the time required for an operator to register multiple ablation sites, but it also saves time by reducing the number of catheter movements required for a given procedure.

Figure 15:
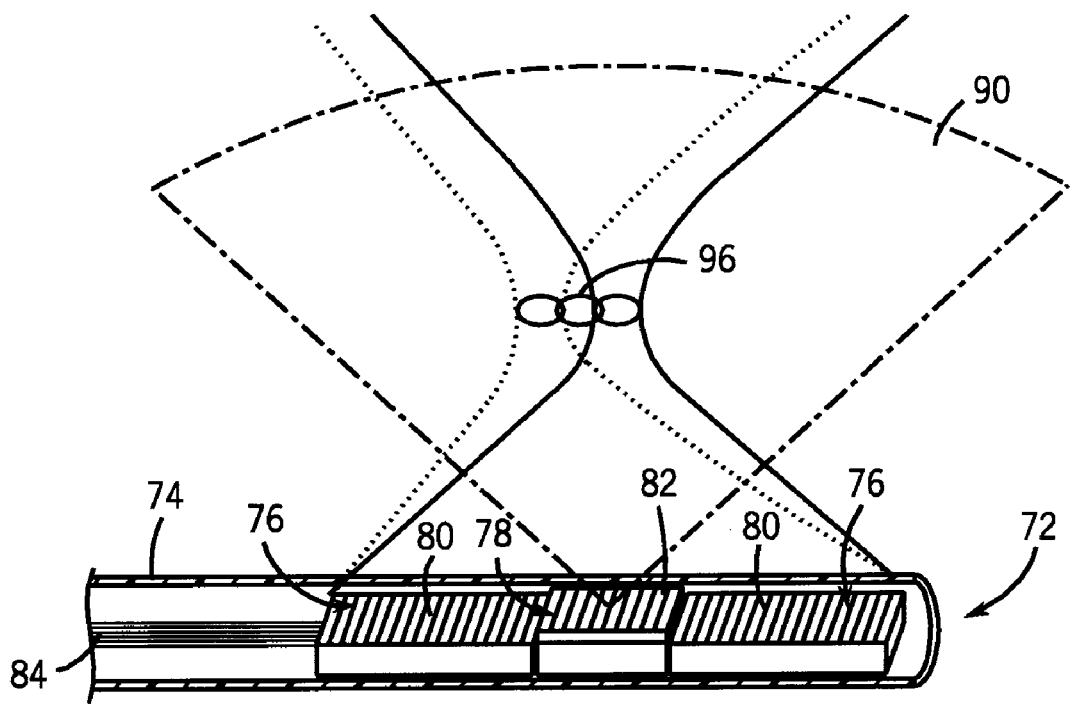
FIG. 15 illustrates an integrated imaging and therapy array in accordance with yet another embodiment of the present invention wherein the imaging array is centered relative to the therapy array.

Referring now to FIG. 15, it is contemplated that the imaging array 78 may be centrally disposed between ablation elements 80 of the ablation array 76. With this construction, the ablation target 96 is centered within the imaged region 90.

In conventional ablation arrays, all the ablation elements are either ON or OFF. In this regard, only the main lobe of the ablation beam is available for ablation. This is the result of grating lobes of the ablation beam being located far off-axis and at a much lower amplitude compared to the main lobe. In accordance with another aspect of the invention, the ablation array is constructed to have switchable ablation elements. In this regard, each ablation element is separately connected to the system controller 23, FIG. 1, and the system controller selectively activates each ablation element as necessary. This selectivity can then be exploited for simultaneous ablation of multiple ablation points. The excitation waveform applied to each element may differ in frequency, phase, time delay, or amplitude from the waveform applied to other elements, in order to control the number, size, shape, and location of the ablation points. In one example, the ablation elements are arranged into sets on a per-ablation basis. By doing so, different excitation waveforms can be generated by the various sets.

Figure 16:
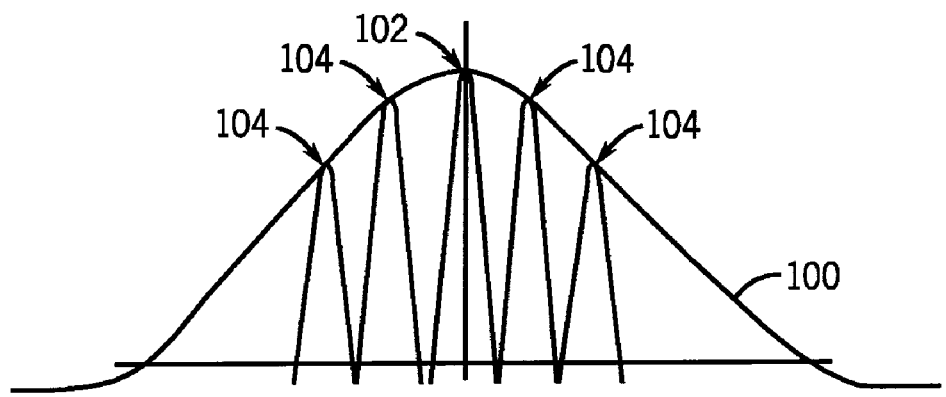
FIG. 16 illustrates an exemplary therapy profile for the exemplary therapy array having one or more deactivated therapy elements that results in a grating lobe that can be used for therapy in addition to a main therapy lobe in accordance with further aspects of the invention.

Referring now to FIG. 16, an exemplary ablation beam profile is shown for an exemplary ablation array having one or more deactivated ablation elements. As shown, the beam profile is characterized by a main lobe 102 and a series of grating lobes 104. The grating lobes 104 have two key differences relative to the grating lobes that result when all the ablation elements are ON. First, the amplitudes of the grating lobes are comparable to the amplitude of the main lobe. Second, the spacing of the grating lobes is relatively narrow. As a result, the grating lobes, in addition to the main lobe, may be used for active ablation. In one example, the combination of the grating lobes with the main lobe results in a linear or curvilinear ablation lesion being created.

Figure 17:
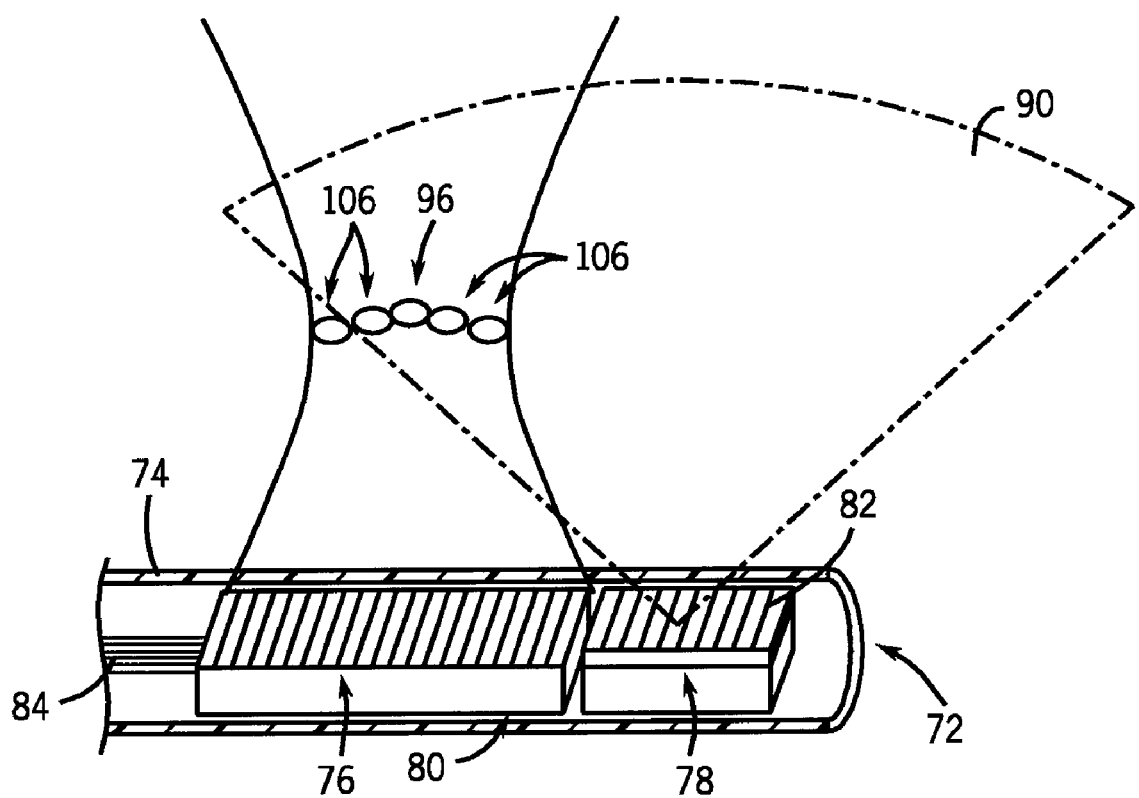
FIG. 17 illustrates the simultaneous treatment of multiple therapy points using a main lobe and one or more grating lobe(s) according to another aspect of the invention.
Figure 18:
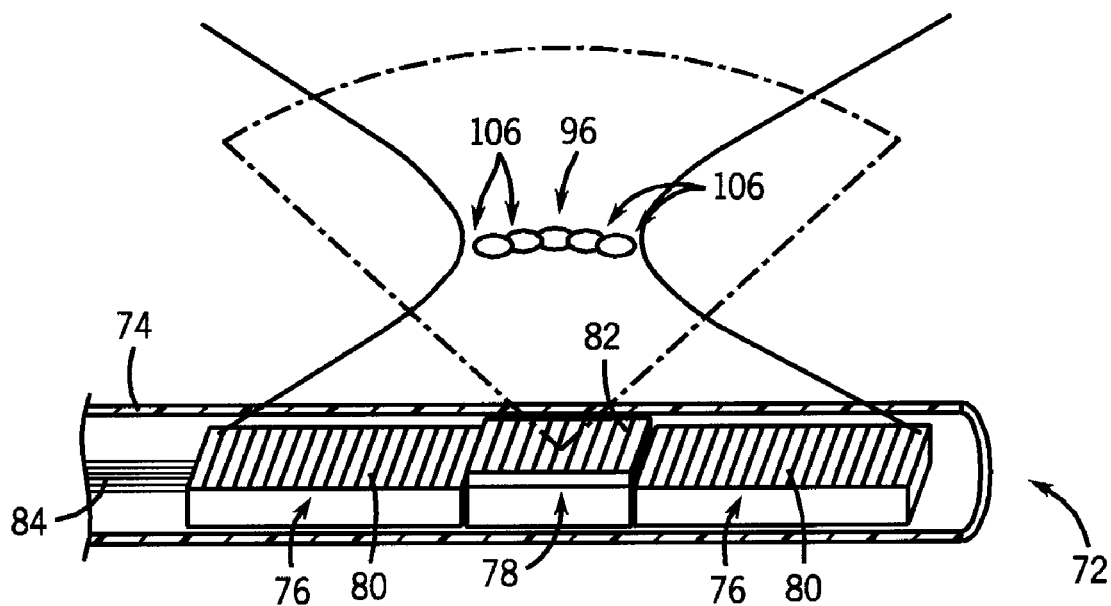
FIG. 18 illustrates the simultaneous treatment of multiple therapy points.

This is illustrated in FIGS. 17-18. In FIG. 17, the integrated ablation and imaging catheter is constructed in a manner described with respect to FIG. 9 with switchable ablation array elements whereas the catheter illustrated in FIG. 18 is constructed in a manner described with respect to FIG. 15 with switchable ablation array elements. Referring now to FIG. 17, the grating lobes created by selectively activating the ablation array elements allow for simultaneous ablation of multiple ablation points, 96 and 106, with the resulting ablation lesion being linear in shape. The central ablation point 96 is ablated by the main lobe of the ablation beam whereas the peripheral ablation points 106 are ablated by the grating lobes. Similarly, in FIG. 18, the main lobe of the ablation beam is used to ablate the central ablation point 96 and the grating lobes are used to ablate the peripheral ablation points 106. In either construction, the central and peripheral ablation points are ablated simultaneously.

Figure 19:
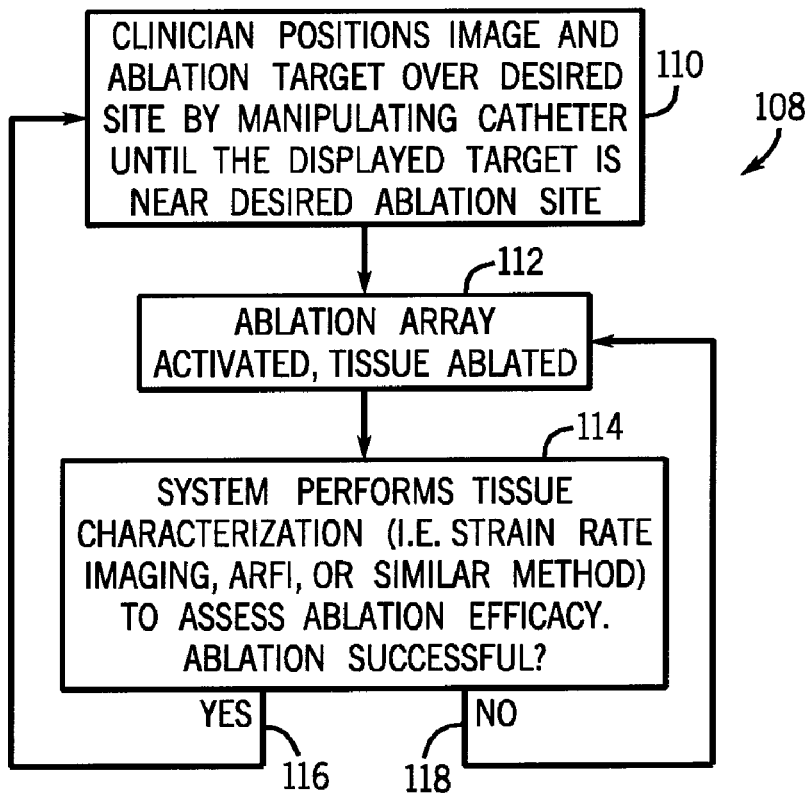
FIG. 19 is a flow chart illustrating an exemplary process for use of an integrated imaging and therapy array according to one aspect of the invention.

In addition to the integrated ablation and imaging catheter heretofore described, the present invention also includes an ablation and imaging process for use with the catheter described. One exemplary process is illustrated in FIG. 19. The process 108 begins at 110 with a clinician translating the catheter through the patient until the desired ablation point is reached. The imaging array acquires and provides real-time images to the clinician that are displayed and used by the clinician to track the position of the catheter. Once the catheter is at or near the ablation site, the ablation site is ablated 112. In a preferred embodiment, before repositioning the catheter, tissue characterization is performed to determine if the ablation was successful 114. The tissue characterization is performed by acquiring and displaying images of the ablation lesion, such as strain rate images, Acoustic Radiation Force Impulse (ARFI) images, or the like. If the ablation was successful 114, 116, the clinician moves the catheter as necessary for further ablation or the process ends. However, if ablation was unsuccessful 114, 118, reablation is performed on the ablation site. Lesion characterization and reablation is reiterated until an acceptable lesion is formed or until the ablation process is halted.

Figure 20:
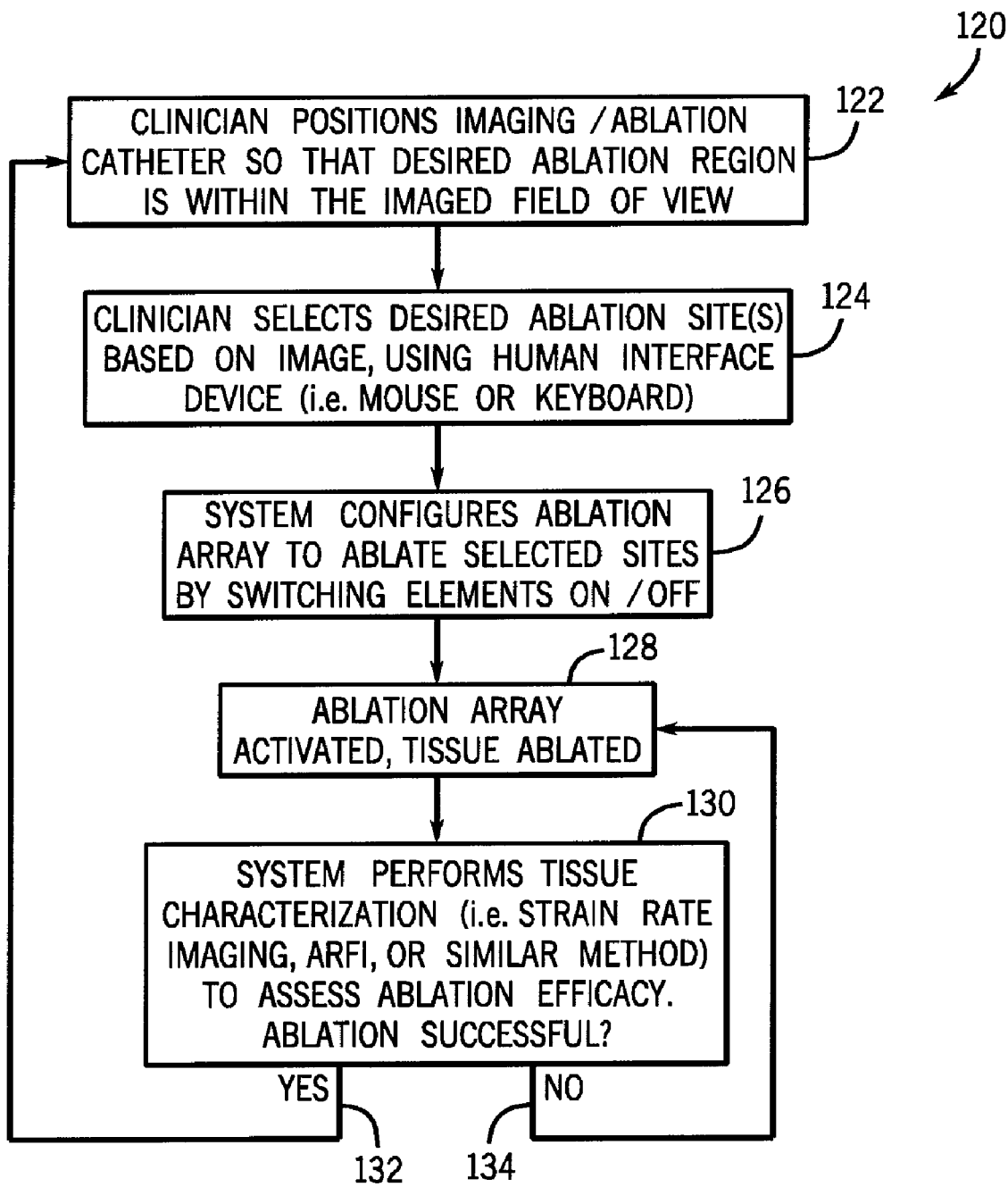
FIG. 20 is a flow illustrating another exemplary process for use of an integrated imaging and therapy array having switchable therapy elements according to another aspect of the invention.

Another exemplary process is illustrated in FIG. 20. In this process, ablation elements are selectively biased to enable simultaneous ablation of multiple ablation sites as described above. The process 120 begins at 122 with a clinician translating the catheter through the patient until the desired ablation point is within the imaged region of the imaging array. The imaging array acquires and provides real-time images to the clinician that are displayed and used by the clinician to track the position of the catheter. Once the catheter is in the imaged region, the clinician identifies the desired ablation sites 124. Based on the selected ablation sites, the ablation elements are selectively activated to enable the simultaneous ablation of the multiple desired sites 126. The activated ablation array then ablates tissue at the various ablation sites 128. Similar to the process described with respect to FIG. 19, tissue characterization is performed at 130. The tissue characterization is performed by acquiring and displaying images of the ablation lesion, such as strain rate images, ARFI, or the like. If the ablation was successful 130, 132, the clinician moves the catheter as necessary for further ablation or the process ends. However, if ablation was unsuccessful 130, 134, reablation is performed on the various ablation sites. Lesion characterization and reablation is reiterated until an acceptable lesion is formed or until the ablation process is halted.

It is contemplated that each ablation site is independently evaluated and, thus, the selectivity of the ablation elements may be altered between applications so that successfully ablated lesions are not reablated during reablation of unsuccessful lesions.

The various methods of imaging and providing therapy and the systems for imaging and providing therapy described hereinabove dramatically enhance efficiency of the process of delivering therapy, such as ablation, by integrating the imaging, therapy, and mapping aspects of the procedure, thereby advantageously eliminating the need for pre-case CT/MRI and static electroanatomical mapping systems. In addition, exposure to harmful ionizing radiation required with current fluoroscopic imaging methods is greatly reduced or eliminated.

Also, the use of the human interface device greatly aids the user in identifying the one or more regions requiring therapy and defining the therapy pathway on the displayed image representative of the imaged anatomical region, rather than having to manually manipulate an RF ablation catheter to physically contact each region on the anatomy to be treated. Consequently, definition of the therapy pathway is greatly improved resulting in lower collateral damage to the tissue of the anatomy being treated. Further, the imaging and therapy transducer with the steerable ablation beam advantageously results in less movement of the imaging and therapy catheter, thereby greatly increasing patient comfort. It is also contemplated that the catheter may be a re-usable or disposable instrument.

Further, employing the techniques of imaging and providing therapy described hereinabove facilitates building cost effective imaging and therapy systems due to reduction in the number of operators required to operate the imaging and therapy system. Current systems require multiple operators to operate each of the ablation system, fluoroscopic imaging system, and the two-dimensional ultrasound imaging catheter, while the imaging and therapy system described hereinabove is configured to image the anatomy and monitor the delivery of therapy with a single device. Furthermore, the imaging and therapy system described hereinabove may be advantageously be operated by a single operator.

Therefore, an ablation device is presented. The ablation device includes an array of ablation elements that are independently controllable. As such, the ablation device further includes a controller connected to the ablation elements and configured to selectively activate the ablation elements for a given ablation procedure.

The invention also includes an integrated therapy and imaging catheter. The catheter is constructed to have an ultrasound imaging transducer and an ablation array having a plurality of ablation elements. The ablation array is constructed such that the ablation elements are selectively activated for multi-lesion ablation.

An imaging and ablation system is also disclosed and comprises a display configured to display images, an imaging device configured to acquire images, and an ablation device having a plurality of independently controllable ablation elements. A controller is operably connected to the imaging device to control image acquisition and is operably connected to the ablation device to selectively activate the independently controllable ablation elements for a given ablation procedure.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An ablation device comprising:
an array of ablation elements, wherein the ablation elements are disposed in one or more rings;
a controller connected to the ablation elements and configured to selectively activate the ablation elements for a given ablation procedure and to steer an ablation beam generated by the array of ablation elements;
wherein the controller is further configured to determine if multiple ablation points are to be ablated and, if so, selectively activate the ablation elements such that the array of ablation elements creates the ablation beam characterized by at least two principal lobes, each lobe used to simultaneously ablate a respective ablation point.

2. The device of claim 1 wherein the controller is further configured to simultaneously steer each of the at least two principal lobes to ablate a respective ablation point.

3. The device of claim 1 wherein the array of ablation elements is disposed within a catheter also having an array of imaging elements disposed therein.

4. The device of claim 3 wherein the array of imaging elements is centrally disposed between a first set of ablation elements and a second set of ablation elements.

5. The device of claim 3 wherein the array of imaging elements is configured to acquire real-time 3D images.

6. The device of claim 3 wherein the controller is further configured to steer the ablation beam to a user-defined location within an imaging volume.

7. The device of claim 1 wherein each ring of ablation elements includes a plurality of ablation sub-elements, each sub-element being independently controlled by the controller.

8. The device of claim 1 further comprising a rotational aid connected to the array of ablation elements and configured to rotate the array of ablation elements.

9. The device of claim 1 wherein the array of ablation elements is tiltable relative to a long axis of a catheter in which the array of ablation elements is disposed.

10. An integrated therapy and imaging catheter comprising:
an ultrasound transducer;
an ablation array having a plurality of ablation elements;
a rotational aid connected to the ablation array of ablation elements and configured to rotate the array of ablation elements;
wherein the plurality of ablation elements are selectively activated for simultaneous multi-lesion ablation;
wherein the ablation array is configured to steer an ablation beam emitting therefrom; and
wherein the ablation beam comprises a plurality of principal lobes, each of the plurality of principal lobes simultaneously steered towards a different ablation point.

11. The catheter of claim 10 further comprising a catheter body and wherein the ultrasound transducer and the ablation array are linearly arranged along a long axis of the catheter body.

12. The catheter of claim 10 wherein the ablation array is spaced apart from the ultrasound transducer.

13. The catheter of claim 10 wherein the ablation array includes a first set of ablation elements spaced from a second set of ablation elements, and wherein the ultrasound transducer is disposed between the first set and the second set of ablation elements.

14. The catheter of claim 10 wherein the ablation array and the ultrasound transducer are independently tiltable relative to one another.

15. The catheter of claim 12 wherein the ablation array is configured to provide a linear or curvilinear ablation lesion.

16. The catheter of claim 12 wherein the ablation array is configured to perform multiple ablations at a single catheter position.

17. The catheter of claim 10 wherein the ablation array is further configured to reablate a given ablation site if a previous ablation is deemed unsatisfactory.

18. The catheter of claim 10 wherein the ultrasound transducer is capable of real-time 3D imaging.

19. The catheter of claim 10 wherein the ultrasound transducer is a 4D mechanically scanning ultrasound transducer.

20. The catheter of claim 10 wherein the ultrasound transducer is a 4D electronically scanning ultrasound transducer.

21. The catheter of claim 10 wherein the ablation array and ultrasound transducer are configured to ablate, assess, and reablate without physical contact with an ablation site.

22. The catheter of claim 10 wherein a frequency response of the ablation array non-overlaps a frequency response of the ultrasound transducer.

23. The catheter of claim 10 wherein a frequency response of the ablation array overlaps a frequency response of the ultrasound transducer.

24. An imaging and ablation system comprising:
a display configured to display images;
an imaging device configured to acquire images;
an ablation device having a plurality of independently controllable ablation elements, wherein the ablation elements are disposed in one or more rings around the imaging device and create an ablation beam characterized by at least two principal lobes; and
a controller operably connected to the imaging device to control image acquisition and operably connected to the ablation device to selectively activate the plurality of independently controllable ablation elements for a given ablation procedure, wherein the controller is configured to automatically assess the efficacy and location of an ablation, and to automatically repeat the ablation if a previous ablation attempt is deemed unsuccessful.

25. The system of claim 24 wherein the imaging device is an ultrasound transducer capable of real-time 3D imaging.

26. The system of claim 24 wherein the imaging device and the ablation device are housed within a common catheter insertable intracorporeally into a subject and wherein the controller is further configured to selectively activate the plurality of indendently controllable ablation elements for ablation of multiple ablation sites at a single catheter position within the subject.

27. The system of claim 24 wherein the controller is further configured to selectively activate the plurality of independently controllable ablation elements to create a linear or curvilinear ablation lesion.

28. The system of claim 24 wherein the controller is further configured to selectively activate the plurality of independently controllable ablation elements to cause ablation of multiple ablation points simultaneously.

29. The system of claim 24 wherein the ablation device includes a first set of ablation elements and a second set of ablation elements spaced from the first set of ablation elements and wherein the imaging device is linearly disposed between the first and the second sets of ablation elements.

30. The system of claim 24 wherein a frequency response of the ablation device overlaps a frequency response of the imaging device.

31. The system of claim 24 wherein a frequency response of the ablation device non-overlaps a frequency response of the imaging device.

32. The ablation system of claim 24 wherein the controller is configured to automatically assess the efficacy and location of an ablation to determine if a previous ablation attempt was unsuccessful using one of strain rate imaging and Acoustic Radiation Force Impulse imaging.

33. An ablation device comprising:
a plurality of ablation elements;
a rotational aid connected to the array of ablation elements and configured to rotate the array of ablation elements; and
a controller connected to the ablation elements and configured to:
define the ablation elements into a first set of ablation elements and a second set of ablation elements for a given ablation procedure, the second set of ablation elements being different from the first set of ablation elements;
overlay a user-defined therapy pathway and an ablation reticle onto a displayed image to provide a view of the pathway and ablation site prior to an ablation;
activate the first set of ablation elements to simultaneously emit an ablation beam, the ablation beam having a plurality of principal ablation lobes; and
independently steer each of the plurality of principal ablation lobes to a different location along the user-defined therapy pathway.

34. The ablation device of claim 33 wherein the controller is further configured to activate the first and second sets of ablation elements but activate the first set differently than the second set.

35. The ablation device of claim 34 wherein the controller is further configured to activate the first set of ablation elements to produce a different excitation waveform than that produced by the second set of ablation elements.

36. The ablation device of claim 35 wherein the controller is further configured to activate the first set of ablation elements to produce an excitation waveform having at least one of a time delay, frequency, phase, and amplitude different than that of an excitation waveform produced by the second set of ablation elements.

37. The ablation device of claim 33 wherein the controller is further configured to redefine the first set and the second set of ablation elements dynamically on a per ablation basis.

38. The ablation device of claim 33 wherein collectively the first and the second sets of ablation elements comprise all the ablation elements of the ablation device.

* * * * *

UNITED STATES PATENT AND TRADEMARK OFFICE
CERTIFICATE OF CORRECTION

PATENT NO. : 7,766,833 B2
APPLICATION NO. : 11/276259
DATED : August 3, 2010
INVENTOR(S) : Lee et al.

It is certified that error appears in the above-identified patent and that said Letters Patent is hereby corrected as shown below:

In Column 18, Line 20, in Claim 26, delete "indendently" and insert -- independently --, therefor.

Signed and Sealed this

Fifth Day of October, 2010

David J. Kappos
*Director of the United States Patent and Trademark Office*